(12) United States Patent
Nath et al.

(10) Patent No.: US 10,408,821 B2
(45) Date of Patent: Sep. 10, 2019

(54) MICROFLUIDIC ASPIRATOR AND METHODS OF MAKING AND USING THE SAME

(71) Applicant: Los Alamos National Security, LLC, Los Alamos, NM (US)

(72) Inventors: Pulak Nath, Los Alamos, NM (US); Jen-Huang Huang, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 0 days.

(21) Appl. No.: 15/488,245

(22) Filed: Apr. 14, 2017

(65) Prior Publication Data
US 2017/0299578 A1   Oct. 19, 2017

Related U.S. Application Data

(60) Provisional application No. 62/322,577, filed on Apr. 14, 2016.

(51) Int. Cl.
*C12M 1/00* (2006.01)
*C12M 3/00* (2006.01)
(Continued)

(52) U.S. Cl.
CPC ......... *G01N 33/5044* (2013.01); *C12M 21/08* (2013.01); *C12M 23/34* (2013.01);
(Continued)

(58) Field of Classification Search
CPC ...... C12M 35/00; C12M 35/04; C12M 29/10; C12M 29/14
See application file for complete search history.

(56) References Cited

U.S. PATENT DOCUMENTS 4,822,741 A * 4/1989 Banes ............... A61L 27/18
427/2.24
5,459,069 A * 10/1995 Palsson ............ C07K 14/535
435/289.1
(Continued)

FOREIGN PATENT DOCUMENTS

WO    WO 2016/049363 A1    3/2016

OTHER PUBLICATIONS

Huang et al., "Non-pneumatic actuation of stretchable membranes with a novel microfluidic aspirator," *EMBS Micro and Nanotechnology in Medicine Conference*, Dec. 12-16, 2016 (1 page).
(Continued)

*Primary Examiner* — Nathan A Bowers
(74) *Attorney, Agent, or Firm* — Klarquist Sparkman, LLP

(57) ABSTRACT

Disclosed herein are devices that include a top chamber including at least one port, a bottom chamber including at least one inlet and at least one outlet, wherein the opening of the at least one inlet is smaller than the opening of the at least one outlet, and a membrane located between the top chamber and the bottom chamber, wherein the membrane is fluidly coupled with the top chamber and the bottom chamber. Also disclosed herein are systems including the disclosed devices. The systems include liquid in one or more of the chambers of the device. Methods of using the devices and systems include producing a vacuum by flowing a liquid through the bottom chamber of the system. Due to the difference in size of the inlet and outlet in the bottom chamber, a vacuum is produced in the top chamber.

20 Claims, 16 Drawing Sheets

(51) Int. Cl.
  *G01N 33/50* (2006.01)
  *C12N 5/071* (2010.01)
  *C12M 1/12* (2006.01)

(52) U.S. Cl.
  CPC .......... *C12M 25/02* (2013.01); *C12N 5/0688* (2013.01); *G01N 33/502* (2013.01); *G01N 33/5014* (2013.01)

(56) References Cited

U.S. PATENT DOCUMENTS

| | | | | |
|---|---|---|---|---|
| 2004/0058408 | A1* | 3/2004 | Thomas | B01L 3/5027 |
| | | | | 435/32 |
| 2004/0132175 | A1* | 7/2004 | Vetillard | C12M 25/16 |
| | | | | 435/297.1 |
| 2006/0270023 | A1* | 11/2006 | LeDuc | C12M 23/20 |
| | | | | 435/289.1 |
| 2009/0088342 | A1* | 4/2009 | Moraes | C12M 23/16 |
| | | | | 506/12 |
| 2011/0129911 | A1* | 6/2011 | Ahluwalia | B01J 19/0073 |
| | | | | 435/289.1 |
| 2014/0127798 | A1* | 5/2014 | Gordon et al. | C12M 23/08 |
| | | | | 435/325 |
| 2017/0335364 | A1* | 11/2017 | Viovy | G01N 33/54313 |

OTHER PUBLICATIONS

Iyer et al., "PulMo: A miniature, tissue-engineered lung," *2016 R&D 100 entry*, Apr. 15, 2016 (38 pages).

\* cited by examiner

MICROFLUIDIC ASPIRATOR AND METHODS OF MAKING AND USING THE SAME

CROSS REFERENCE TO RELATED APPLICATION

This claims the benefit of U.S. Provisional Application No. 62/322,577, filed Apr. 14, 2016, which is incorporated herein by reference in its entirety.

ACKNOWLEDGMENT OF GOVERNMENT SUPPORT

This invention was made with government support under Contract No. DE-AC52-06NA25396 awarded by the U.S. Department of Energy. The government has certain rights in the invention.

FIELD

This disclosure relates to devices for creating a vacuum and methods of making and using the same, such as to mimic lung function.

BACKGROUND

Lung diseases are some of the most common medical conditions in the world, and are caused by factors such as smoking (including second-hand smoke), infections, and genetics. A key issue with pharmaceuticals is that approximately 90% of candidate drugs fail clinical trials due to lack of efficacy and/or toxicity. Even some pharmaceuticals that pass clinical trials are later found to have serious side effects. Furthermore, there are thousands of compounds whose effects are currently unknown that could be potentially useful therapeutic compounds.

SUMMARY

In accordance with one aspect of certain embodiments, a need exists for devices that can more accurately mimic lung function and provide an environment similar to that of a lung for uses such as drug toxicology and/or efficacy screening, disease modeling, and the like. Disclosed herein are exemplary embodiments that can more accurately mimic lung physiology, including breathing mechanics and flow dynamics.

Certain embodiments are also useful for creating a "chip-scale" (e.g., microfluidic) vacuum or reduction in pressure. In addition, embodiments can also be used as flow and/or viscosity sensors for microfluidic or millifluidic scale uses.

In accordance with an embodiment, an apparatus or device includes a top chamber including at least one port and a bottom chamber including at least one inlet and at least one outlet. A flow restriction is provided at and/or upstream of the outlet, such as providing a reduction in cross sectional area of the flow path at the location of the restriction. The restriction can be upstream of the inlet or at the one or more inlets. That is the total cross sectional area of all of the inlets or other restriction is less than the total cross sectional area of all of the outlets. If there is only one inlet and one outlet, the opening (cross sectional area) of the inlet can be smaller than the opening (cross sectional area) of the outlet. The inlet can be a portion or section of the bottom chamber. By pumping liquid from the bottom chamber, as a result of this restriction, the pressure drops in the bottom chamber relative to the top chamber and creates a vacuum in the top chamber. In contrast, reducing or stopping the fluid flow increases the pressure in the bottom chamber relative to the pressure prior to such reduction or stoppage of fluid flow. As a result, if the port is open to the atmosphere, the reduction of pressure in the bottom chamber draws or inhales air into the top chamber and the relative increase in pressure in the bottom chamber pushes or exhales air out through the port. In accordance with this embodiment, a membrane can be located between the top chamber and the bottom chamber, wherein the membrane has a side that is fluidly coupled with the top chamber and a side that is fluidly coupled with the bottom chamber. The terms fluidly coupled or fluidically coupled means in fluid communication with. The term fluid includes gas or liquid. In some embodiments, the devices include at least one substrate located between the top chamber and the bottom chamber. The substrate can include one or more openings across which the membrane extends, wherein the substrate has a side that is fluidly coupled with the top chamber, a side that is fluidly coupled with the bottom chamber, and/or a combination thereof. A second substrate can also be placed over the first substrate with the membrane sandwiched therebetween. The use of upper and lower substrates facilitates the use of extremely thin membranes as the substrates reinforce the membranes other than at openings through the substrates. The second substrate can also have one or more openings desirably aligned (overlaying at least in part or entirely) the one or more openings of the first substrate.

In accordance with an aspect of certain embodiments, the membrane can include or support at least one population of cells associated with a side of the membrane. For example, a first population of cells associated with the side that is fluidly coupled with the top chamber. The membrane can also include or support a second population of cells associated with the side that is fluidly coupled with the bottom chamber.

As a further aspect of certain embodiments, the apparatus can include a plurality of substrates stacked together, for example including a top substrate including at least one port, a vacuum chamber substrate including a top chamber portion, a liquid flow chamber substrate including at least one inlet and at least one outlet; and a bottom substrate. The device can also include one or more membrane substrates and a membrane located between the vacuum chamber substrate and the liquid chamber substrate. In some examples, the device includes a first (top) membrane substrate having one or more openings wherein a side of the first membrane substrate is fluidly coupled with the top chamber portion and a second membrane substrate having one or more openings, wherein a side of the second membrane substrate is fluidly coupled with the liquid chamber. The membrane in this example can be located between the first and second membrane substrates with at least a portion of a first side of the membrane in contact with the first membrane substrate and at least a portion of the first side of the membrane is fluidly coupled with the top chamber portion. In addition, at least a portion of the second side of the membrane opposite to the first side is in contact with the second membrane substrate and at least a portion thereof is fluidly coupled with the bottom chamber.

In an alternative embodiment, the top chamber can be interposed between a third chamber that is like the bottom chamber with a membrane positioned between the third chamber and top chamber. One or more membrane supporting substrates, with respective openings there through as discussed above can also be provided in this latter embodiment.

Also disclosed herein are systems including the disclosed devices. The systems can include liquid in one or more of the chambers of the device. In some examples, the system includes liquid in the bottom chamber and air or gas in the top chamber. In other examples, the system includes liquid in the top chamber and liquid in the bottom chamber. If there is liquid in both chambers, the liquid in each chamber can be the same or different. In some examples, the liquid in the bottom chamber is a liquid cell culture medium, for example in embodiments of the disclosed devices including at least one population of cells associated with a side of the membrane.

Methods of using the devices and systems are also disclosed. In some embodiments, the methods include producing a vacuum by flowing a liquid through the bottom chamber of the device or system. In some examples, the methods include alternately or selectively starting and stopping and/or reducing the flow rate of a liquid in the bottom chamber, thereby alternately creating and releasing and/or reducing a vacuum in the upper chamber. In some embodiments, for example when the top chamber contains air or gas, the methods produce air or gas flow into the top chamber in response to a vacuum in the top chamber (for example, through the port in the top chamber) and air or gas flow out of the top chamber (for example, through the port) when the vacuum is released. Thus, in some examples, the disclosed devices, systems, and methods can provide a model of the physiological function of breathing.

Also disclosed herein are lung organ systems that include the disclosed aspiration devices as an integrated component. In some embodiments, a lung organ system includes a bronchiolar device fluidly coupled to a disclosed aspirator device (for example, via the port in the top chamber. In additional embodiments, the lung organ system can include additional components such as fluid management system(s) or circuit(s), pump(s), valve(s), tubing, connectors, and/or reservoirs.

In accordance with additional aspects an embodiment of an apparatus according to this disclosure can comprise a housing comprising a top chamber comprising at least one port and a bottom chamber comprising at least one inlet and at least one outlet. The bottom chamber can have a first section connected to the inlet, a second section connected to the outlet, and at least one intermediate section between the inlet and the outlet. In addition, the cross sectional area of the first section is smaller at a first location than at a second location spaced further from the at least one inlet than the first location, and wherein the cross sectional area of the second section is smaller than at a third location than at a fourth location positioned nearer to the at least one outlet than the third location. For example, the cross sectional area at the first section can progressively increase moving away from the inlet, such as by diverging side walls, and the cross sectional area of the second section can progressively decrease moving toward to outlet, such as by converging side walls, to thereby control the flow into the intermediate section and from the intermediate section to the outlet to produce a more uniform pressure change across the first and second sections and to reduce the possibility of air bubbles being trapped in the bottom chamber. In addition, the membrane comprises a boundary edge and first and second side surfaces, at least a portion of the first side surface of the membrane being fluidly coupled to the bottom chamber and at least portions of the second surface of the membrane being fluidly coupled to the top chamber.

As another aspect of an embodiment, the cross sectional area of the inlet, and all of the inlets if there is more than one inlet, can be less than the cross sectional area of the at least one intermediate section.

As yet another aspect of an embodiment, the bottom chamber can have a bottom chamber top wall that comprises a first membrane supporting first substrate positioned to support the first side surface of the membrane, the first membrane supporting first substrate comprising at least one first substrate opening into which the membrane expands in response to a pressure drop in the bottom chamber relative to the pressure in the top chamber. In addition, a second substrate can overlay the first substrate. The second substrate can comprise at least one second substrate opening aligned with the at least one first substrate opening. In response to the elimination and/or reduction of the pressure drop in the bottom chamber relative to the pressure in the top chamber, the membrane moves toward the at least one second substrate opening.

In accordance with a further aspect of an embodiment, the at least one port can be open to the atmosphere such that expansion of the membrane into the first substrate opening inhales air into the top chamber from the atmosphere and movement of the membrane toward the at least one second substrate opening exhales air outwardly from the top chamber through the port. A population of cells can be provided on at least a portion of at least one of the first and second side surfaces of the membrane and the bottom chamber can contain a liquid cell culture medium for nurturing the cell population.

In accordance with further aspects of embodiments, a source of liquid such as liquid cell culture medium can be coupled to the at least one inlet and a pump can be coupled to the at least one outlet. The apparatus comprises an upstream to downstream liquid flow path from the source of liquid downstream to the at least one inlet, through the bottom chamber to the at least one outlet and from the at least one outlet to the pump. In addition, the flow path has a section of reduced cross sectional area at or upstream of the inlet to the bottom chamber or upstream of intermediate section of the bottom chamber. In a first pump state, the pump operates to pump the liquid from the at least one outlet of the bottom chamber and reduces the pressure in the bottom chamber relative to the pressure in top chamber so that the membrane moves into the first substrate opening and inhales air from the at least one port into the upper chamber if the port is open. In a second pump state the pump stops pumping or reduces the flow rate of the liquid from the at least one outlet of the bottom chamber; which increases the pressure in the bottom chamber relative to the pressure in the bottom chamber when the pump is in the first pump state. As a result, the membrane moves toward the at least one second substrate opening and exhales air outwardly from the upper chamber through the at least one port if the port is open. The pump can be cycled between the first and second pump states a plurality of times to cause the repeated inhaling of air through the at least one port into the top chamber and the exhaling of air from the top chamber through the at least one port. The rate of cycling can be varied. The apparatus can therefore mimic lung function (breathing). In addition, a population of alveolar cells can be positioned on one or both sides of the membrane and the membrane can have pores to facilitate cell nutrients passing through the membrane to the cells.

The disclosure also encompasses methods as found in this disclosure, including a method of maintaining a population of cells along at least one surface of a membrane. This method can comprise supporting a membrane having first and second sides between top and bottom chambers with the first side in fluidic communication with the bottom chamber and the second side being in fluidic communication with the top chamber, at least one of the sides of the membrane supporting the population of cells; pumping liquid cell culture medium through the bottom chamber to reduce the pressure in the bottom chamber and expand the membrane into the bottom chamber; stopping the pumping of liquid cell culture medium through the bottom chamber to thereby relax the membrane and move the membrane toward the top chamber; and inhaling air into the top chamber in response to the expansion of the membrane into the bottom chamber and exhaling air from the top chamber in response to the relaxation of the membrane.

By coupling a pressure regulator to the port in communication with the top chamber, the apparatus can be used for determining viscosity and flow rates.

Also, by incorporating a lens into the lower chamber, the focal point of the lens can be changed by controlling the flow rate through the lower chamber to thereby provide a tunable lens.

The foregoing and other features of the disclosure will become more apparent from the following detailed description, which proceeds with reference to the accompanying figures.

DETAILED DESCRIPTION

I. Explanation of Terms

Figure 1:
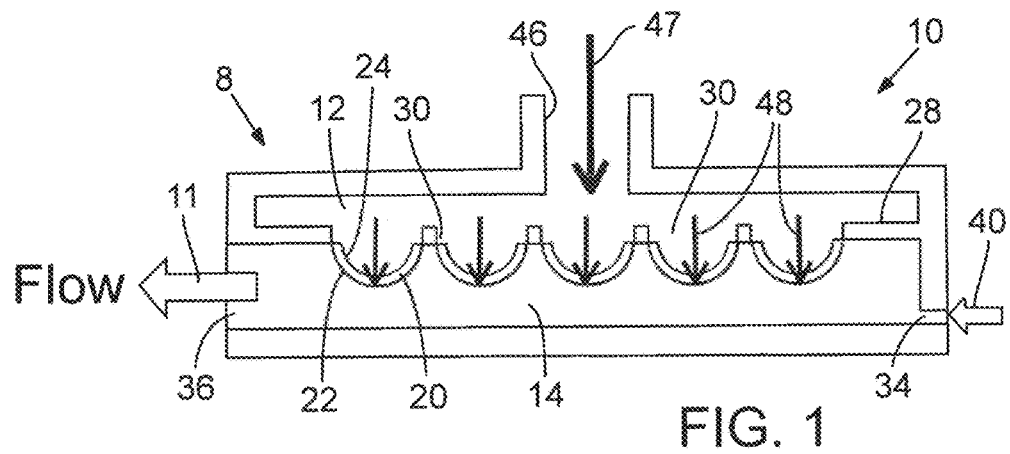
FIGS. 1 and 2 are schematic illustrations showing cross-sectional views of an exemplary embodiment of a disclosed aspirator device in a flow ("inhale") configuration (FIG. 1) and a stop flow ("exhale") configuration (FIG. 2).

The following explanations of terms are provided to better describe the present disclosure and to guide those of ordinary skill in the art in the practice of the present disclosure. As used herein, the words "including" and "having" and their formatives have the same meaning as "comprising and its corresponding formatives. Also, the singular forms "a" or "an" or "the" include plural references unless the context clearly dictates otherwise. The term "or" refers to a single element of stated alternative elements or a combination of two or more elements, unless the context clearly indicates otherwise. The term "coupled to" (e.g. element A is coupled to element B) includes direct connection of the elements and also includes indirect connection of the elements through one or more other elements.

Any theories of operation are to facilitate explanation, but the disclosed devices, materials, and methods are not limited to such theories of operation. Although the operations of some of the disclosed methods are described in a particular, sequential order for convenient presentation, it will be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed components and materials can be used in conjunction with other components and materials. Additionally, the description sometimes uses terms such as "produce" and "provide" to describe the disclosed methods.

These terms are high-level abstractions of the actual operations that are performed. The actual operations that correspond to these terms will vary depending on the particular implementation and are readily discernible by one of ordinary skill in the art.

In some examples, values, procedures, or devices are referred to as "lowest," "best," "minimum," or the like. It will be appreciated that such descriptions are intended to indicate that a selection among many used functional alternatives can be made, and such selections need not be better, smaller, or otherwise preferable to other selections.

Examples are described with reference to directions indicated as "above," "below," "upper," "lower," "top", "bottom" and the like. These terms are used for convenient description, but do not imply or require any particular spatial orientation. For example, if an apparatus has two chambers and can be oriented with a first chamber above the second chamber, the first chamber that is above the second chamber can be called a top chamber. If the orientation is changed such that the chambers are vertical or reversed with the second chamber above the first chamber, the apparatus still has a top chamber (the first chamber is still a top chamber, even though it is now oriented on the bottom). The term "and/or" is to be broadly construed to include all possible combinations of elements or items with which the term is used, as well as the elements or items individually.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims. Furthermore, not all alternatives recited herein are equivalents.

II. Device Embodiments

Disclosed herein are devices that can be utilized to create a vacuum, for example, in a microfluidic environment. As discussed below, the devices can be used to simulate breathing without using air pumps to introduce air into the device, and by producing mechanical stretch of the membrane (and any associated cells) without using pneumatic sources. In addition to providing a more physiological model, the disclosed devices reduce instrumentation complexity, simplify operation, and reduce cost compared to current lung models.

In the disclosed devices, the membrane component is actuated to produce mechanical stretch of the membrane and create a reduction in pressure or a vacuum in the top chamber. Briefly, liquid is flowed through the bottom chamber of the device. A restriction is provided in the flow path such as at an inlet or upstream from the inlet to the bottom chamber. The restriction has a smaller cross sectional area than the liquid outlet, and a smaller cross sectional area than the total cross sectional area of all of the outlets if more than one outlet. For example, the restriction can be positioned upstream from the aspirator in a liquid flow path or incorporated into the one or more inlets, such as by providing inlets with a total cross sectional area that is less that the cross sectional area of the outlets. The inlet can, for example, be internal to the aspirator or at the entrance to the aspirator bottom chamber. When the liquid is pumped from the outlet, a pressure drop is created in the bottom chamber, creating a pressure drop or vacuum in the top chamber resulting from an expansion of the membrane into the lower chamber ("into" includes "toward"). As a result, the membrane(s) stretch into the bottom chamber. If there is an open port in the top chamber, the vacuum produces air or gas intake or inhaling (or fluid movement into the top chamber). When flow in the bottom chamber is stopped, or the flow rate is reduced, the pressure drops in the bottom chamber. For example, if the flow is stopped, pressure in the bottom chamber equilibrates causing the membrane(s) to relax back to their starting position (or to substantially their starting position). If there is an open port in the top chamber, the pressure equilibration produces air or gas outflow or exhaling (or fluid movement out of the top chamber, if the top chamber contains fluid). The pressure drop in the lower chamber can be controlled by controlling the pumping rate of liquid out of the lower chamber, although stopping and starting the pump is a desirable option to control inhaling into and exhaling from the top chamber. The pressure in the bottom chamber can alternatively be caused to rise more rapidly in the bottom chamber by reversing the pump to pump liquid through the outlet and into the lower chamber.

FIG. 1 depicts an embodiment 8 of an apparatus in a first operating (liquid is flowing through the bottom chamber in the direction indicated by arrow 11 configuration. The FIG. 1 apparatus includes a housing 10 having a top chamber 12, a bottom chamber 14 and a membrane 20. The membrane comprises an edge boundary and opposed first and second major side surfaces. In FIG. 1, the first side surface 22 faces toward bottom chamber 14 and the second side surface 24 faces the top chamber 12. The membrane 20 is positioned in this embodiment between top chamber 12 and bottom chamber 14. The side 24 of membrane 20 is fluidly coupled with top chamber 12 and the side 22 of membrane 20 is fluidly coupled with bottom chamber 14. In some examples, the apparatus desirably also includes a first substrate 28 between top chamber 12 and bottom chamber 14. Substrate 28 includes one or more openings, some of which are indicated at 30 in FIG. 1. The membrane 20 spans these openings. Although not shown in the schematic view of FIG. 1, typically the membrane is continuous across all of the openings. In some embodiments, as discussed below, membrane 20 is sandwiched between two substrate layers. The example depicted in FIG. 1 is an embodiment with five openings or wells 30 in substrate 28.

The device also includes at least one liquid inlet 34 and at least one liquid outlet 36. The outlet 36 is desirably located at a different side or end of the bottom chamber 14 from the inlet 34, for example, in a wall of the bottom chamber opposite to inlet 34. Although the embodiments illustrated herein show inlet 34 and outlet 36 as being substantially aligned and on opposite ends of the bottom chamber, additional configurations can be utilized, including having the inlet and outlet on opposite sides of the bottom chamber, but not aligned with one another or having the inlet and outlet on adjacent sides of the bottom chamber and/or extending upwardly through the top of the bottom chamber from opposite ends of the bottom chamber. In the example of FIG. 1, inlet 34 is smaller (for example in diameter or cross-sectional area) than outlet 36 and thus is one example of a constriction in the liquid flow path. Arrow 40 illustrates the flow of liquid into the lower chamber 14 through the inlet 34. The inlet and outlet may have any cross-sectional shape, including circular, rectangular, square, oval, or other shapes.

Top chamber 1 in FIG. 1 also can include a port 46, which in some embodiments is an air or gas inlet/outlet port. The port 46 in FIG. 1 communicates with top chamber 12. In FIG. 1, the port 46 is depicted on the upper (top) surface of the top chamber, but the port can be located at any position on the top or side surfaces of the top chamber or otherwise to communicate with the top chamber. In some embodiments, top chamber 12 contains air or gas and bottom chamber 14 contains a liquid. As discussed below, during the flow of a liquid through bottom chamber 14 from inlet 34 to outlet 36, arising from pumping liquid from outlet 36, a pressure drop is created in the bottom chamber, resulting in a vacuum or pressure reduction in top chamber 12. In response to the pressure drop in the bottom chamber, the membrane 20 expands into the openings 30 toward the bottom chamber and can, in some embodiments expand into the bottom chamber. This draws or inhales air or gas (as indicated by arrow 47) into the port 46. The deforming of membrane 20 toward, and in this example into, the bottom chamber 14 through the openings 30 in response to the pressure drop is illustrated by the arrows 48.

Figure 2:
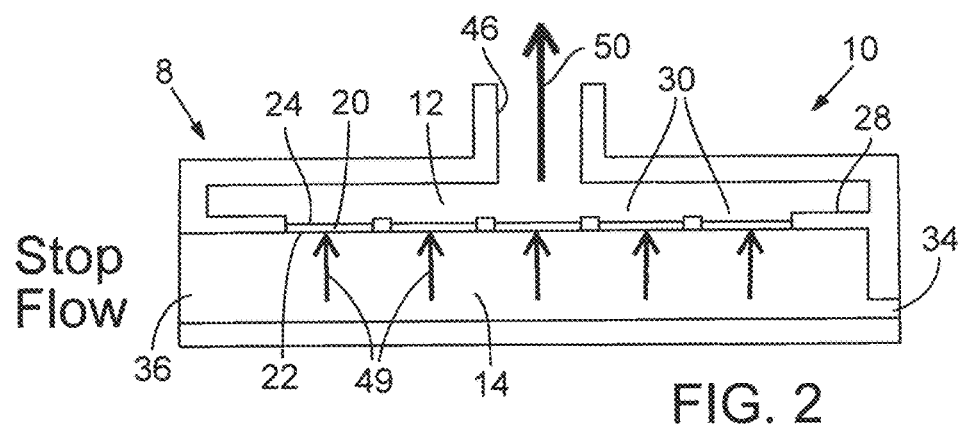

FIG. 2 depicts the FIG. 1 embodiment in a resting (stop flow) position. When there is no flow or a reduced flow through bottom chamber 14, the pressure in the the chamber is in equilibrium with the pressure in the upper chamber, if for example the upper chamber is at ambient pressure. Under these conditions, the membrane 20 moves toward the top chamber, as indicated by arrows 49, and the membrane achieves a relaxed position as shown in FIG. 2. In response to this relaxation of membrane 20, and assuming the upper port 46 is coupled to the atmosphere, gas is pushed out of the upper chamber 12 (exhales) as indicated by arrow 50. The pressure in the bottom chamber can be repeatedly decreased and increased to create inhaling and exhaling breathing cycles to mimic lung function. Although specific embodiments of the devices are illustrated herein, the number positioning, size, and shape of inlet(s), outlet(s), port(s), and openings in the device and the size and shape of the chambers are only exemplary. Additional configurations can also be utilized and are within the scope of this disclosure.

Figure 3:
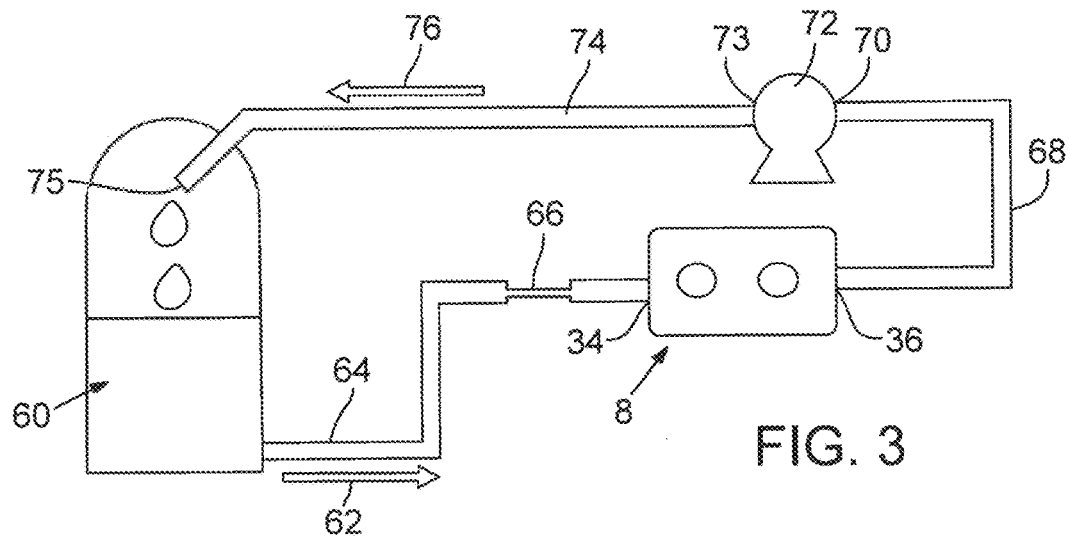
FIG. 3 is a schematic illustration of a pump system including a source of liquid and a flow path through an exemplary embodiment of an aspirator.

FIG. 3 illustrates and exemplary system including an aspirator in accordance with this disclosure, such as the aspirator 8. In FIG. 3, a source of liquid 60 is shown, such as a supply tank which can be maintained in sterile conditions and that can be included in a closed loop system. A fluid flow path is provided from upstream source 10 in a downstream direction indicated by arrow 62. The fluid flow path in this example includes a first tubing section 64 from source 60 to aspirator inlet 34. In this example, the flow restriction is included in tubing section 64 and is shown at 66 at a location upstream from the inlet 34. In this case, the inlet 34 may or may not include a further restriction to liquid flow. The liquid enters inlet 34 and flows through the bottom chamber or chambers of the aspirator 8 to the outlet 36. From outlet 36, the flow path includes a second tubing section 68 that communicates with the inlet 70 of a pump 72. The outlet 73 of pump 72 communicates with a tubing section 74 leading to an inlet 7a5 to the source 60. Downstream flow in tubing section 74 is indicated by the arrow 76.

To increase the exhaling rate, the flow of liquid can be reversed to flow into the outlet of the lower chamber and cause a more rapid rise in pressure in the lower chamber. By cycling this pump between forward liquid flow (out from the outlet) and reverse liquid flow (into the outlet), the inhale/exhale rate can be increased such as to mimic a lung breathing during running or other strenuous exercise. To keep the flow of fresh nutrient containing liquid cell media into the lower chamber, the forward flow cycle can be longer than the reverse flow cycle to have a net forward mass flow rate of liquid through the bottom chamber. For example, the forward flow can be for three seconds and reverse flow for two seconds. When the pump is in a pump on or first pumping state, liquid is pumped at a first rate from outlet 36 of the aspirator 8 and causes the pressure drop in the bottom chamber of the aspirator. When the pump is in a second state with the pump off or pumping at a rate that is slower than the pumping rate in the first state, or in a reverse flow direction, the membrane in aspirator 8 relaxes or moves toward the upper chamber as the pressure increases in the lower chamber (e.g. as the pressure drop in the bottom chamber is relieved). The pump can be cycled between the first and second pumping states to repeatedly cause inhaling and exhaling from the top chamber of the aspirator. In addition, the pump can be cycled between states at variable and periodic rates to mimic breathing. Also, the pumping rate can be varied, using for example, a variable speed pump, to control the amount of the pressure drop in the bottom chamber and control the volume of inhaled and exhaled gas from the top chamber. The pump can also be a reversible flow pump that can pump liquid from the outlet 36 or pump liquid into the outlet. The pump can be responsive to control signals to control the pumping flow rate, pumping direction and and duration of pumping times.

Although they can be the same, the duration of forward flow and reversed, reduced and/or stop flow rate times do not need to be the same. For example, one can have forward flow for three seconds followed by stopping forward flow for five seconds; for example to allow the membrane to relax and move toward the top chamber.

Figure 4:
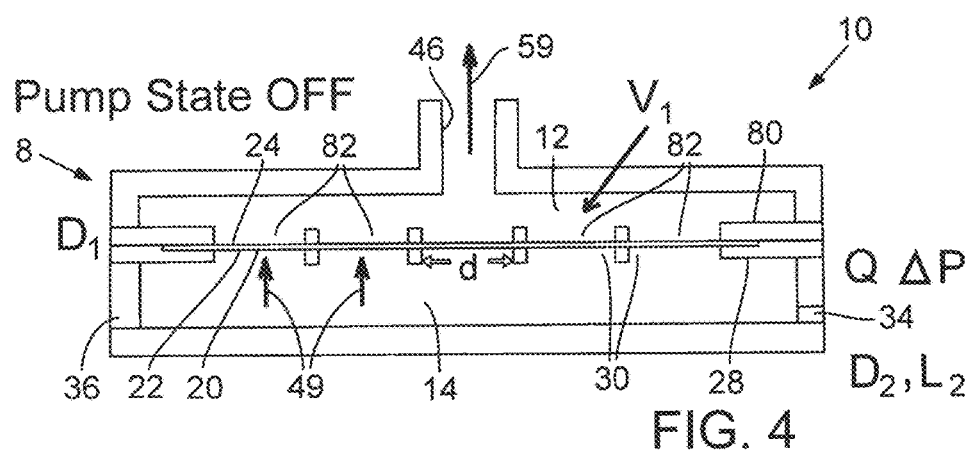
FIGS. 4 and 5 are a schematic illustrations showing cross-sectional views of an exemplary embodiment of the disclosed microfluidic aspirator indicating various parameters in a Pump OFF state (FIG. 4) and a Pump ON state (FIG. 5).
Figure 5:
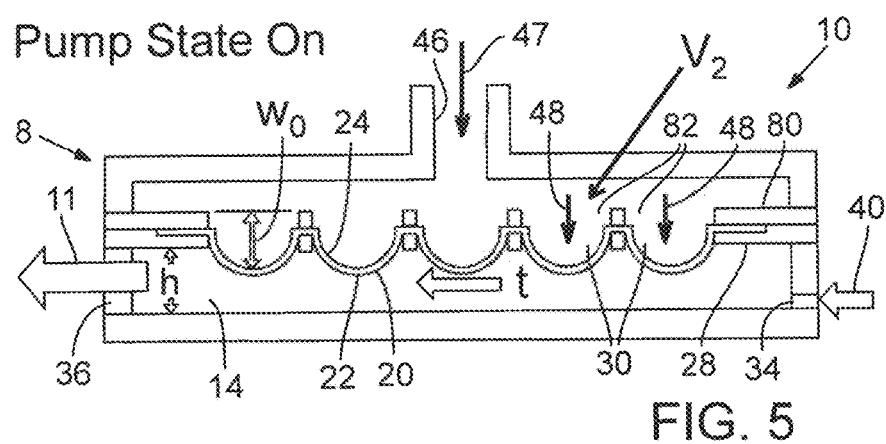

FIG. 4 is similar to FIG. 2 in that it illustrates the pump off state and FIG. 5 is similar to FIG. 1 in that it illustrates the pump on state. In FIGS. 4 and 5, an upper substrate 80 is shown between top chamber 12 and the membrane 20. The substrate 80 has one or more openings (five in the example of FIGS. 4 and 5), several of which are indicated by the number 82. The openings 82 are aligned with the openings 30 in the substrate 28, that is openings 82 overlay openings 30 at least in part, and more desirably entirely, to facilitate expansion of the membrane toward the lower chamber in the pump on state due to the reduced relative pressure in the lower chamber in comparison to the pressure in the upper chamber. In FIGS. 4 and 5, the membrane is not shown to scale as it is typically very thin such that there is no need for a recess in the top surface of the substrate 28 to accommodate the membrane and there is desirably no gap between the top surface 24 of membrane 20 and the bottom surface of substrate 80 or between the bottom surface 22 of membrane 20 and the top surface of substrate 28. This is true of other embodiments disclosed herein where the membrane is shown for convenience as having a thickness that makes it seem like a gap between the substrate surfaces and the membrane is present. However, if desired, such a gap can be provided.

Various parameters of the aspirator device are identified as follows: h=bottom chamber height in an embodiment where the bottom chamber has a constant height, such as by a plate of height h; d=diameter of openings over which membrane is stretched in the example circular openings; E (not indicated in these figures)=elasticity of membrane, which affects how fast the membrane returns to its relaxed position if pumping of liquid from the outlet is stopped; $D_1$=Diameter of outlet in the example a circular outlet; $D_2$=Diameter of inlet in the example of a circular inlet; $L_2$=Length of inlet restriction (time) in the example where the inlet restriction is formed in the housing 10 leading to the lower chamber; $V_1$=volume of the top chamber in a pump resting (off) state; $V_2$=volume of the top chamber after deflation (the pump in a pump on state); $w_0$=deflation height, the height to which the membrane expands toward the lower chamber; Q=flow rate; $\Delta P$=pressure drop caused by restriction of fluid flow; $\tau$=shear stress on the membrane; and f=frequency of pumping (e.g. the cycling rate between off and on states). These use of these variables is explained below.

In some examples, $D_1$ is greater than $D_2$, where the restriction is in the inlet. Thus, in some embodiments, the ratio of $D_1/D_2$ is greater than 1 (such as 1.1-50, 1.5-10, 2-15, 3-20, 4-25, 5-30, 8-40, or 10-50), for example, about 2, 3, 4, 5, 6, 7, 8, 9, 10, 12, 15, 20, 25, 30, 35, 40, 50, or more. In one non-limiting example, the ratio of $D_1/D_2$ is about 10. In embodiments where the inlet and/or outlet are not circular in cross-section and the restriction is at the inlet, the ratio of the cross-sectional area of the outlet to the cross-sectional area of the inlet is greater than 1 (such as 1.1-50, 1.5-10, 2-15, 3-20, 4-25, 5-30, 8-40, or 10-50), for example, about 2, 3, 4, 5, 6, 7, 8, 9, 10, 12, 15, 20, 25, 30, 35, 40, 50, or more. A ratio of 10 to 1 is one specific example. These same ratios desirably apply to the total cross sectional area of all outlets to the total cross sectional area of all inlets and also desirably apply to the ratio of the cross sectional area of all outlets to the cross sectional area of a restriction located upstream of the aspirator 8, for example in a liquid supply line upstream of the inlet. The pressure drop is in general proportional to the ratio of the total cross sectional area of all outlets to: (a) the total cross sectional area of all inlets if the restriction is included at the inlet; or (b) the cross sectional area of the restriction if upstream from the inlet. The higher the ratio, the larger the pressure drop in response to a given flow rate, and also the larger the deflection of the membrane for a given flow rate. The port in the top chamber can be eliminated if desired.

Figure 6:
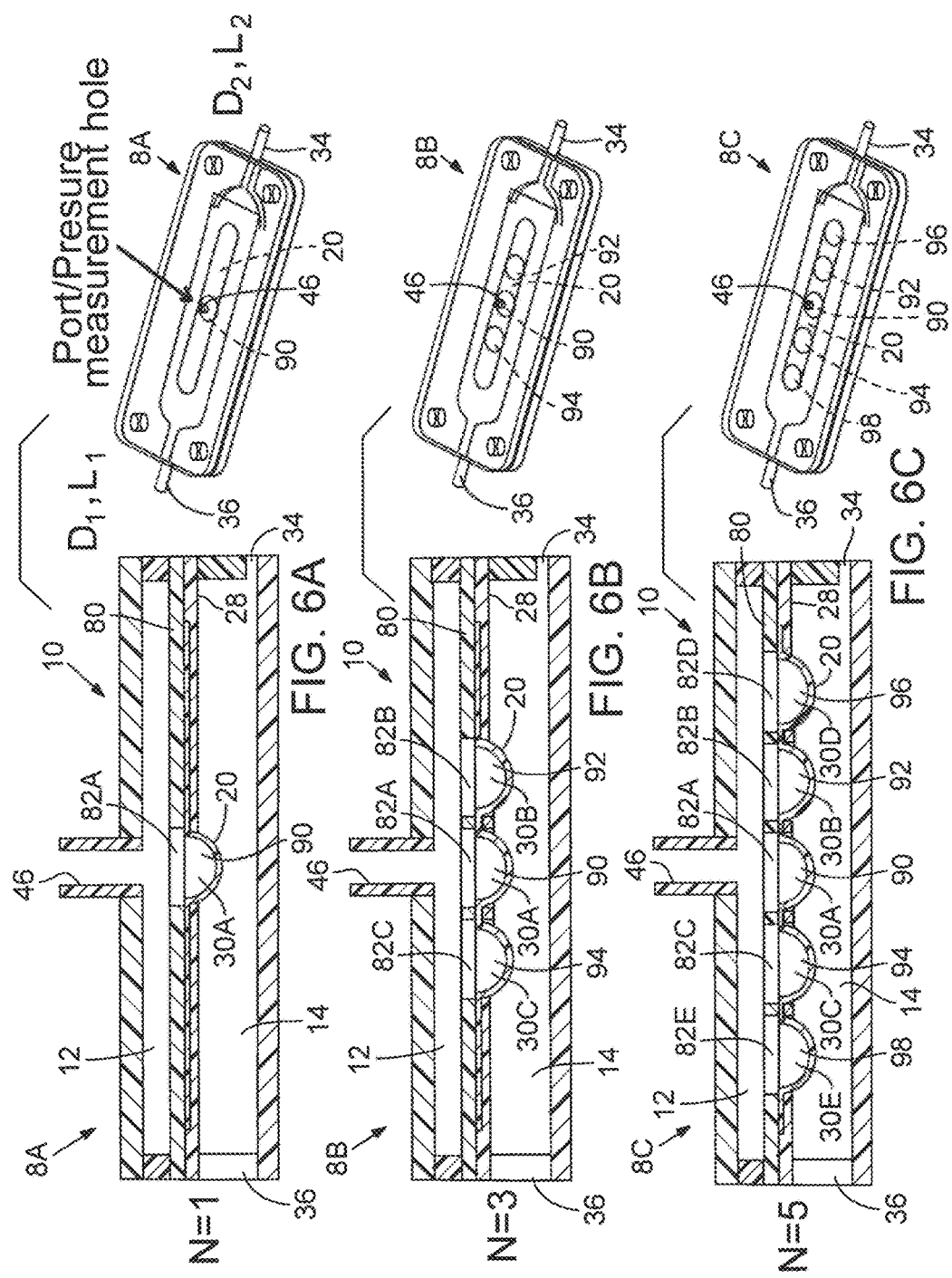
FIGS. 6A-6C are a series of schematics illustrations of exemplary cross-sectional (left) and perspective (right) views of embodiments with increasing numbers of membrane expansion wells and increasing membrane expansion surface area, such as one well (FIG. 6A), three wells (FIG. 6B), and five wells (FIG. 6C). The wells comprise membrane-covered openings between top and bottom chambers. In the cross-sectional views of these embodiments, the port in the top chamber is not shown in the cross sectional views for convenience, but may be present (for example, as shown in the perspective views of each of these FIGS.).

FIGS. 6A, 6B and 6C illustrates three exemplary aspirator apparatus embodiments; respectively with increasing membrane expansion surface area. Numbers for elements in these FIGS. that correspond to the numbers in FIGS. 1, 2 4 and 5 have been included in FIGS. 6A-6B and will not be discussed further. In some cases a letter has been added to an element for convenience in describing the embodiments (e.g. 30A corresponding to an opening 30 in FIG. 1, 2, 3 or 4).

The exposed membrane surface area is a function of the number of openings in the substrate between the top and bottom chambers, and also the size of the openings. In the embodiments shown in FIGS. 6A-6C, the aspirator respectively includes 1, 3, or 5 membrane-covered openings or wells. The single well 90 of the aspirator of FIG. 6A is defined by openings 30A and 82A in the respective substrates 28 and 80. The three wells 90, 92 and 94 of the aspirator of FIG. 6B are respectively defined by openings 30A, 82A; 30B, 82B; and 30C, 82C in the substrates 28, 80. The five wells 90, 92, 94, 96 and 98 of the aspirator of FIG. 6C are respectively defined by openings 30A, 82A; 30B, 82B; 30C, 82C; 30D, 82D; and 30E, 82E in the substrates 28, 80. However, any number of openings can be utilized, such as 1-50 openings or more, with a 96 well or opening device being one desirable example. Other examples include 1-10, 3-12, 5-15, 10-20, 15-30, 25-40, or 30-50 openings. In other examples, the device includes more than 20 openings (such as more than 50, more than 100, more than 200, more than 400, more than 500, or more. In some non-limiting examples, the devices include 1, 3, 5, 8, or 16 openings; however, any number of openings can be selected, depending on the size of the device and the particular use. In addition, the openings can be arranged in any configuration, such as linearly, in a grid, circularly, radially, or other arrangements, such as in a bronchial or branched pattern.

The size of the openings can be selected based on the desired use of the device. In some embodiments, the openings are about 1-100 µm in diameter (such as about 1-10, 3-15, 5-20, 10-50, 25-60, 40-80, or 50-100 µm diameter). In other examples, the openings are more than 100 µm in diameter, such as 200 µm, 400 µm, 500 µm, 750 µm, 1 mm, 2 mm, 4 mm, 5 mm, 10 mm, 20 mm, or more in diameter. One specific example is 4 mm. In addition, while round (circular) openings are used in some exemplary embodiments illustrated herein, other shapes, including oval, square, rectangular, or other shapes can also be used.

The membranes 20 utilized in the disclosed devices are flexible, and in some examples, porous (for example, to permit diffusion of nutrients from the liquid chamber to cells located on the air chamber side of the membrane). In some embodiments, the membrane material is an elastic, polymeric material capable of resilient deformation and reformation (e.g., such as expanding to form a semi-sphere and contracting back to its original shape, or resting state, such as the shape it retains when no external force is exerted on the material to force it to expand). The material, however, should not be so elastic as to lose its shape over an extended period of time (e.g., time periods ranging from hours to days to weeks to months). In some non-limiting examples, the membranes are polyurethane polydimethylsiloxane (PDMS), latex, or rubber membranes. However, any material suitable for thin membranes can be used, including poly-L-lactic acid, polycaprolactone (PCL), PLLA-PCL copolymer, polyester, polycarbonate, or a combination thereof.

In some examples, the thickness of the membrane ranges from 1 to 100 µm, such as 1 to 50 µm, or 1 to 10 µm. In exemplary embodiments, the membrane is about 10 µm thick with 10 µm and 35 µm thick membranes being specific examples. In examples where the membrane has pores, such as to provide nutrients to cells supported by (associated with) the membrane, the diameter of the pores of the membrane have diameters that can range from 0.4 to 12 µm, such as 0.4 to 3 µm, or 0.4 to 1 µm, with pore densities ranging from $1\times10^5$ to $1\times10^8$ pores/cm$^2$, such as $4\times10^5$ to $4\times10^6$ pores/cm$^2$, or $2\times10^6$ to $4\times10^6$ pores/cm$^2$. In exemplary embodiments, the pores have a diameter of about 3 µm. The term about when used in this disclosure includes values within plus or minus five percent of the stated value. The membrane may be pore free, such can be the case in examples where the device is being used in viscosity and flow rate determinations and vacuum pump applications.

Figure 7:
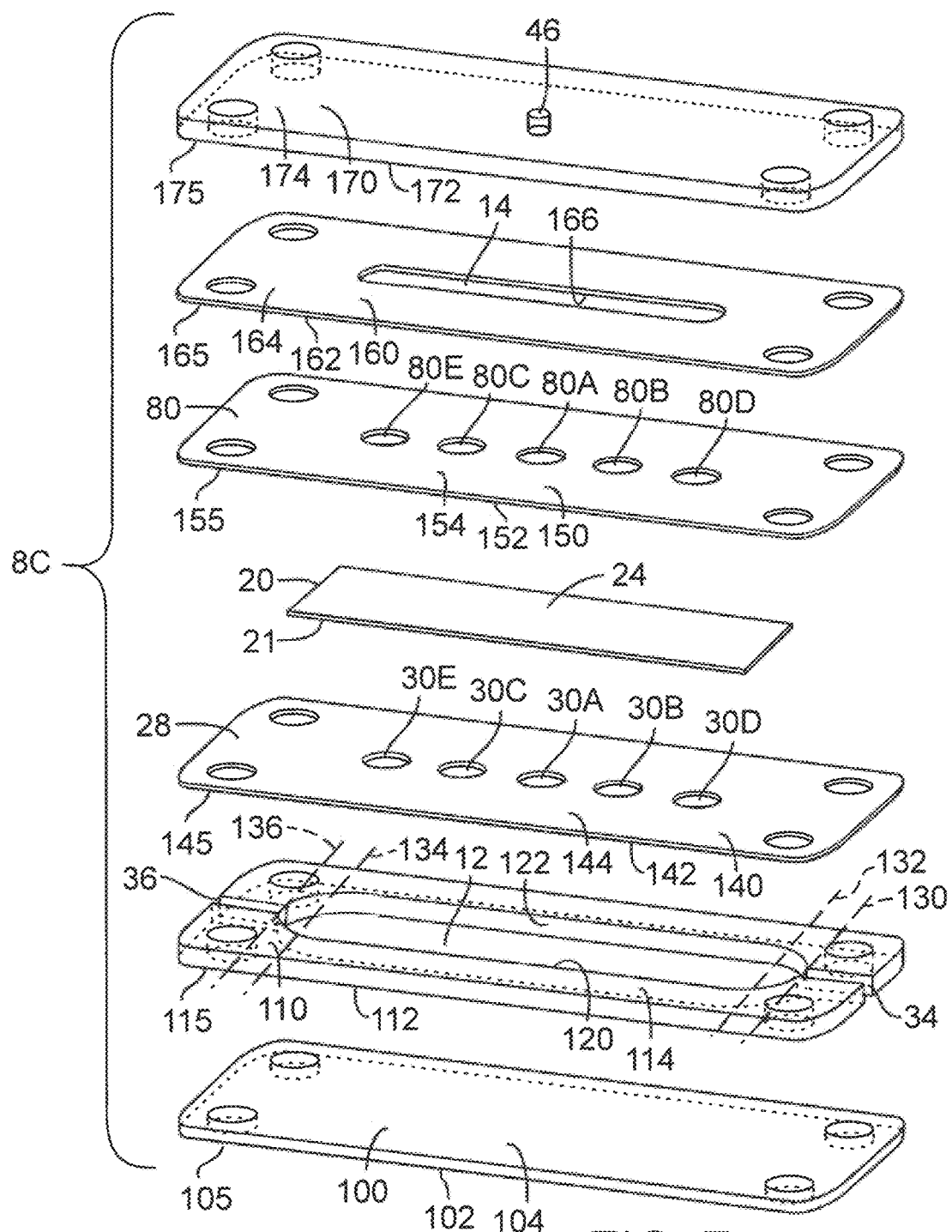
FIG. 7 is an exploded view of an exemplary aspirator apparatus of the form shown in FIG. 6.0 showing the layers (also referred to as substrates) used to make this exemplary device.

FIG. 7 is an exploded view of an exemplary device like that of FIG. 6C made by stacking or laminating a plurality of substrates (also referred to as layers). The other embodiments can also be made in the same manner. The substrates making up the various layers can be in the form of plates with opposed major surfaces and side edges that are stacked and held in place by adhesive, registration pins or otherwise secured together. More or fewer substrates that those shown in FIG. 7 can be included in the aspirator, such as additional intermediate plates or substrates.

In the embodiment of FIG. 7, the apparatus comprises a bottom chamber bottom wall substrate 100 with opposed top and bottom surfaces 102, 104 and a peripheral side edge 105. The top surface 104 bounds or closes the bottom of the bottom chamber 14 in this example.

The embodiment of FIG. 7 also comprises a bottom chamber intermediate substrate 110 overlaying the bottom chamber bottom wall substrate 100. The substrate 110 has a bottom surface 112, a top surface 114 and a peripheral edge 115. The bottom surface 112 is coupled to and can abut surface 104 of substrate 100 in the assembled aspirator. The substrate 110 has bottom chamber side walls 120, 122 that surround a hollow opening between the top and bottom surfaces 114, 112 that defines the side boundaries of the illustrated bottom chamber 14. The inlet 34 and outlet 36 communicate with the chamber 14 through respective end portions of the walls 120, 122 in this example.

The illustrated chamber 14 formed by plate 110 has a first section extending longitudinally from inlet 34, and more specifically from the location where inlet 34 enters chamber 14, to a location 132; a second section extending longitudinally from a location 134 to a location 136 at the outlet 36, and more specifically at the location where outlet 36 exists the chamber 14; and at least one intermediate section extending longitudinally between locations 132 and 134. The intermediate section in this example has a constant cross sectional area and underlies the membrane receiving openings in substrates positioned above the substrate 110. These sections are also shown in the FIGS. 13 and 14 embodiment, but are of a different configuration.

Figure 8:
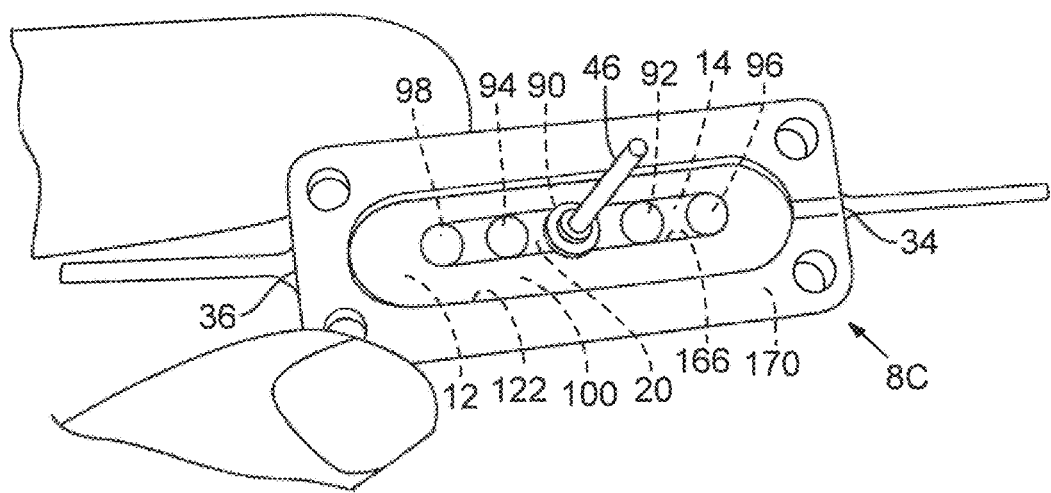
FIG. 8 is a top perspective view of a five well aspirator of FIG. 7, the five wells being visible through the top chamber in this embodiment.

In the illustrated FIG. 7 example, the cross sectional area of the first section is smaller at a first location (e.g. at location 130) than at a second location (e.g. at location 132) spaced further from the at least one inlet 34 than the first location. In addition, the cross sectional area of the second section is smaller at a third location (e.g. at location 136) than at a fourth location (e.g. at location 134) positioned further from the at least one outlet than the third location. In the embodiment of FIG. 7 (and also in the embodiment of FIGS. 13 and 14 discussed below), at least portions of the first and second side walls 120, 122 bounding the first section can diverge from one another moving away from the at least one inlet 34. In addition, in these embodiments, at least portions of the first and second side walls 120, 122 bounding the second section can converge toward one another moving toward the at least one outlet. In the embodiment of FIGS. 7 and 8, and of FIGS. 13 and 14, the cross sectional area of the first section progressively increases moving away from the inlet and the cross sectional area of the second section progressively decreases moving toward the outlet. In the FIGS. 13 and 14 embodiment, the side walls 120, 122 taper toward one another in the first section moving longitudinally toward the inlet and the side walls 120, 122 also taper toward one another in the second section moving longitudinally toward the outlet.

The illustrated side walls 120, 122 in these exemplary embodiments assist in preventing air or gas bubbles from being trapped in the chamber 14 as the chamber is filled and/or during operation of the aspirator. In addition, these side wall constructions also assist in establishing a more gradual transition in pressure changes in liquid as it enters and leaves the intermediate section.

With continued reference to FIG. 7, a bottom chamber top wall substrate 140 having bottom and top surfaces 142, 144 and a peripheral side edge 145 overlays the bottom chamber intermediate or bottom chamber defining substrate 110. The substrate 140 comprises the plurality of spaced apart openings 30A-30E positioned above the bottom chamber 14 when the aspirator is assembled. The surface 142 of substrate 140 is coupled to and can abut surface 114 of substrate 110 in the assembled aspirator. The top surface 144 of substrate 140 is positioned below and is coupled to and can engage, e.g. abut, the bottom surface 22 of the membrane 20 in the assembled aspirator with the membrane 20 overlaying the openings 30A-30E. The membrane 20 has a peripheral edge 21 extending between the bottom and top membrane surfaces 22, 24.

A top chamber bottom wall substrate 150 has bottom and top surfaces 152, 154 and a peripheral edge 155. The substrate 150 has the plurality of spaced apart openings 80A-80e overlaying and coupled to the top surface 24 the membrane and also respectively overlaying the spaced apart openings 30A-30E of the substrate 140 of the assembled aspirator.

In addition, a top chamber intermediate substrate 160 is shown that has bottom and top surfaces 162, 164 and a peripheral edge 165 the substrate 160, has a longitudinally elongated, oval in this example, top chamber 12 opening extending through the substrate and bounded or surrounded by a side wall 166. The substrate 160 is positioned to overlay substrate 150 with the top chamber 12 overlaying the openings 80A-80E in this example. When assembled, the bottom surface 160 of substrate is coupled to and can abut the top surface 154 of substrate 150. A top chamber top substrate 170, having bottom and top surfaces 172, 174 and a peripheral edge 175 overlays substrate 160 and closes the top chamber 14. The surface 172 is coupled to and can abut the surface 164 of the substrate 160. In addition, a port 46 is shown and communicates through substrate 170 and with the top chamber 40 in this example.

The apparatus in this example thus includes top layer 170 with a port 46; vacuum chamber layer 160 with top chamber 12, top substrate 150 with openings 82A-82E; membrane 20; bottom substrate 140 with openings 30A-30E; liquid chamber layer 110 with a bottom chamber 14, inlet 34, and outlet 36; and a bottom layer 100. In this embodiment, the membrane is sandwiched between a top substrate 150 and bottom substrate 140. In addition, in this embodiment the respective openings 82A-82E and 30A-30E in the top and bottom substrates are substantially aligned with one another and have substantially the same size and shape. The apparatus can also include one or more alignment holes such as shown at each corner of each layer other than the membrane in FIG. 7, which can receive registration pins to assist with proper layer alignment during assembly of the device.

FIG. 8 illustrates an assembled aspirator of FIG. 7. The layers, or a plurality of such layers on at least one side of the membrane, can be transparent so that the functioning of the aspirator can be observed externally.

Figure 9:
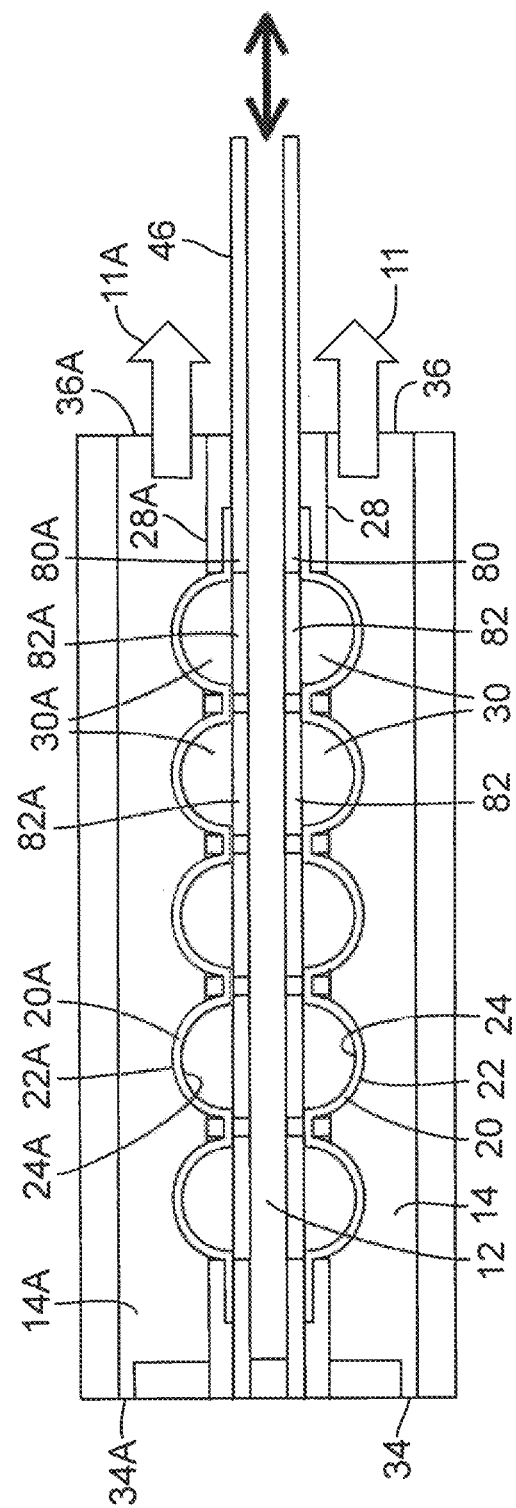
FIG. 9 shows a schematic diagram of an exemplary integrated two membrane aspirator embodiment with a central top chamber and two outer liquid flow chambers.
Figure 10:
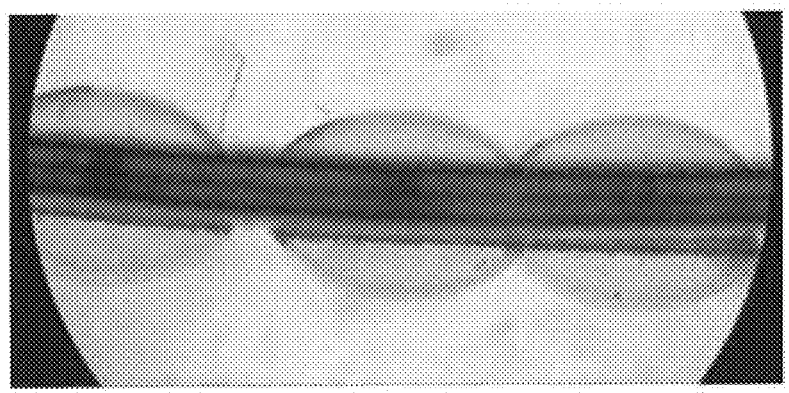
FIG. 10 is an image of the embodiment of FIG. 9 showing inflated "alveoli" supported by the membranes of this embodiment.
Figure 11:
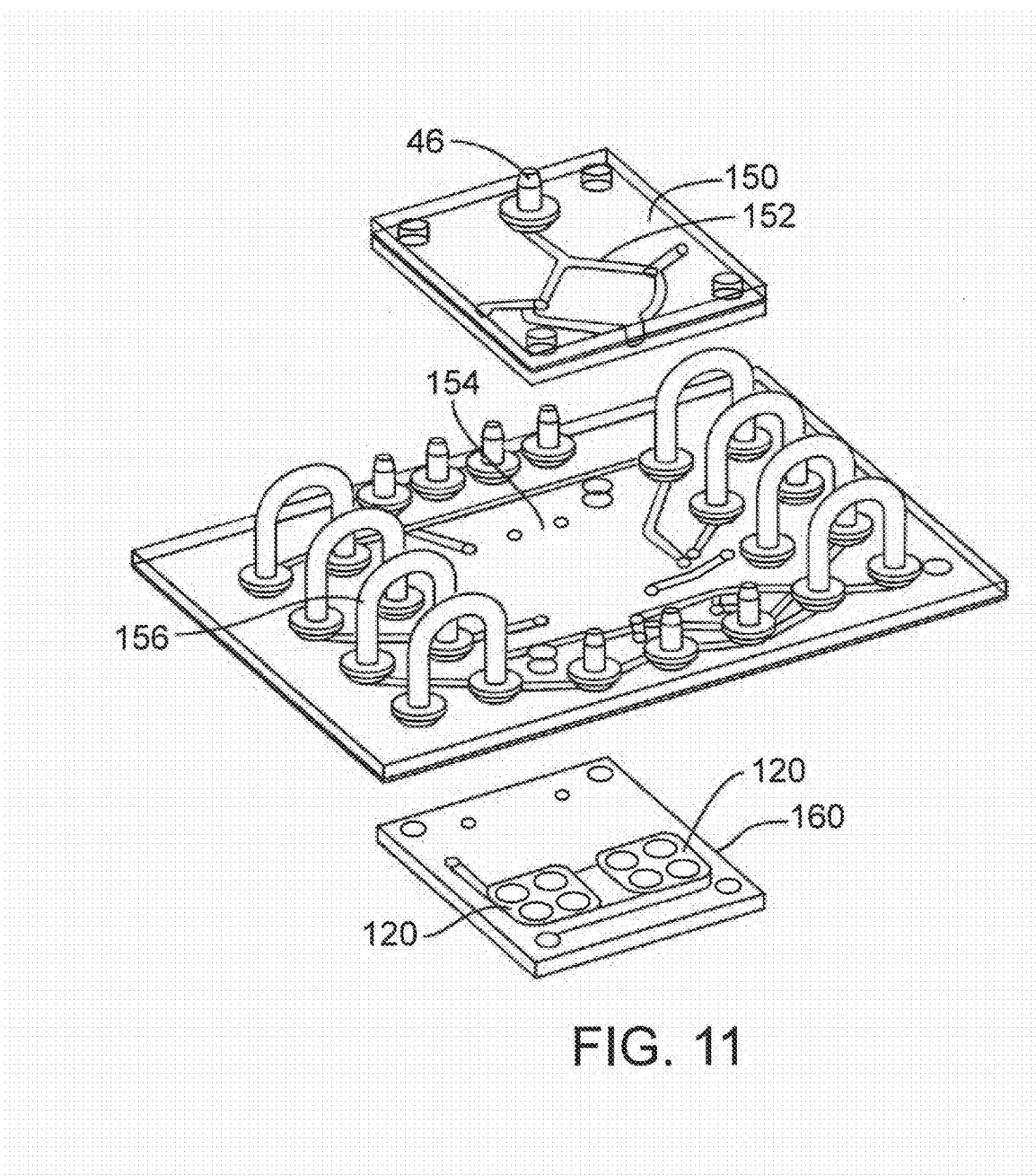
FIG. 11 is a perspective view of an exemplary lung device including an embodiment of an aspirator as disclosed herein.

In some embodiments, two of the disclosed devices can be integrated to form a device embodiment. In some examples, the devices share an air or gas chamber (referred to as the "top" chamber for example in the embodiments of FIGS. 1 and 2) and a single or common port for air or gas intake and release. An example of this construction is illustrated in FIG. 9, the device includes two liquid chambers 14, 14A, each with an inlet 34, 34A and an outlet 36, 36A. In some embodiments, the inlet 34 can be smaller in cross sectional area that the outlet 36 and the inlet 34A can be smaller in cross sectional area than the outlet 36A to provide the constriction as described above. Alternatively, the constriction can be positioned upstream of the aspirator such as, for example, in liquid supply tubing connected to the inlets. The embodiment of FIG. 9 has a single shared air or gas chamber (top chamber) 12, and a shared air or gas port 46. Elements of the lower liquid chamber in FIG. 9 are numbered as previously described, while elements of the second liquid chamber (the second bottom chamber) are given the same numbers, but with the letter A following the number. These elements will not be discussed further as they have been described above. This FIG. 9 embodiment provides a more physiologically relevant model of lung alveoli, as shown in the image in FIG. 10 of inflated "alveoli".

In various embodiments, the device can further include a plurality of cells on the surface 24 of membrane 20 facing the top chamber 12 and/or on the surface 22 of membrane 20 facing the bottom chamber 14. In some embodiments, one side of the membrane material is associated with a first population of cells and the other side of the membrane material is associated with a second population of cells. The first population of cells is associated with a side of the membrane material that is fluidly coupled with top chamber 12 and the second population of cells is associated with a side of the membrane material that is fluidly coupled with bottom chamber 14. In some examples, the first population of cells includes immune responsive cells, surfactant-producing cells, or a combination thereof, and the second population of cells includes pulmonary microvascular cells. In exemplary embodiments, the first population of cells includes alveolar type 1 (AT1) cells, alveolar type 2 (AT2) cells, or a combination thereof and the second population of cells includes human lung microvascular endothelial cells, human lung smooth muscle cells, human lung fibroblast cells, monocytes, dendritic cells, or a combination thereof (such as A549 cells, H441 cells, AT1, and/or AT2 cells).

The device may further include additional components, such as a pump 72, described in connection with FIG. 3 above, for providing liquid flow through the bottom chamber or liquid flow chamber or chambers. In some examples, the device includes a pump (such as a peristaltic pump) fluidly coupled to the outlet 36 in the bottom chamber of the device. In other examples, the device is integrated into a larger microfluidic unit or system.

In some embodiments, the devices disclosed herein are integrated into a lung organ platform or system. In some examples, the disclosed device is utilized as an alveolar device that is fluidly coupled (directly or indirectly) to one or more bronchiole devices (such as a bronchiole device disclosed in International Pat. App. Publ. No. WO 2016/049363, incorporated herein by reference in its entirety). In particular embodiments, the bronchiole device is fluidly coupled to the port 46 in the top chamber 12 of the disclosed devices. A bronchiolar device includes a device or system that can be used to mimic a bronchiole airway system of a lung for use in testing for toxicity and/or efficacy of particular drugs, as well as to investigate various diseases, such as pulmonary disease. In some examples, a bronchiolar device has at least two micro-channels (a form of chambers) separated by a membrane. The topside-channel 12 can be filled with media and airway epithelial cells for cell seeding and maintenance. The one or more outlets of the bottom-side-channel 14 is connected to a pump, which can be filled with different media. When connected to an alveolar device (such as the devices disclosed herein), the topside-channel 12 is connected to the alveolar unit, whereas the bottom-side-channel is connected to the pump to provide media circulation. In some examples, a bronchiolar device includes a plurality of channels that are arranged in a branching configuration, to more closely mimic lung physiology. Exemplary bronchiolar devices are illustrated in FIGS. 8A and 8B herein, and are described in more detail in International Pat. App. Publ. No. WO 2016/049363.

Figures 12, 13:
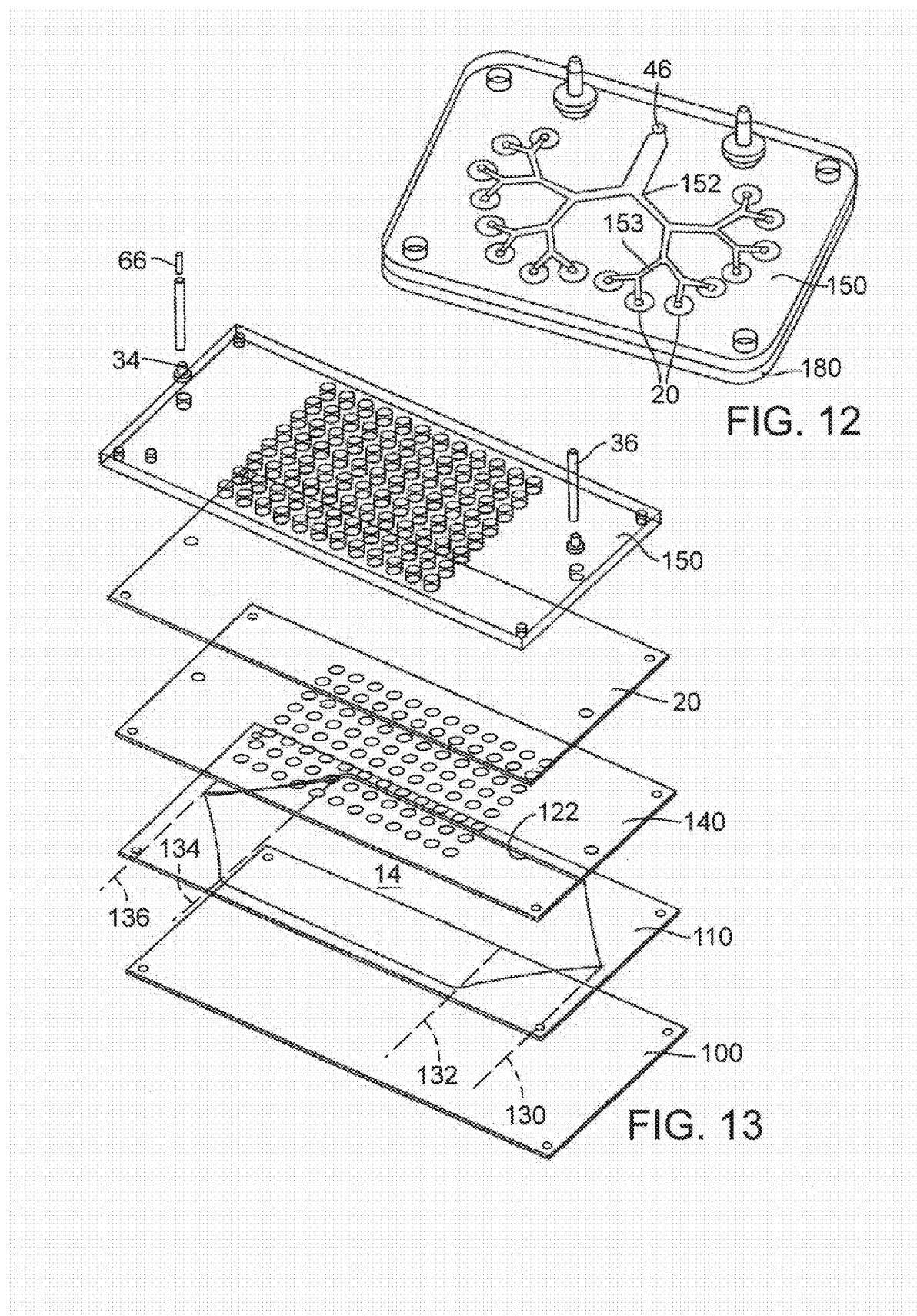
FIG. 12 is a schematic illustration of an alternative embodiment of an exemplary lung device including an embodiment of an aspirator as disclosed herein.
FIG. 13 is an exploded view of an exemplary ninety-six well embodiment of an aspirator in accordance with this disclosure.

Lung device or apparatus (also referred to as an alveolar device or apparatus) can incorporate aspirators as disclosed herein. One example of a lung apparatus is shown in FIG. 12. This apparatus includes a bronchiole unit 150; a branched microchannel network 152 mimicking or recapitulating branching in a human lung with a port 46, the microchannel network 152 being an exemplary top chamber 12; a multilayer microchannel network 154 for fluid management between bronchiole and alveolar units (for delivering liquid to the lower chambers of the apparatus to cause inhaling and exhaling through the port 46); valves, such as pinch valves 156, for flow switching and management to control the flow of liquid (e.g. from a source in response to pumping by a pump) to lower chambers of the device; and an alveolar device 160 of the present disclosure including membranes 20 and one or more liquid flow (bottom) chambers with respective inlets and outlets, as previously described, that can be cyclically stretched using microfluidic aspiration as described herein to breathe air or gas in/out of the port 46 of the lung apparatus.

In some embodiments, a lung organ platform includes one or more of the disclosed devices (also referred to as alveolar device(s)) fluidly coupled to one or more bronchiole devices, and one or more fluid management systems (such as a fluid circuit board disclosed in International Pat. App. Publ. No. WO 2016/049365, incorporated herein by reference in its entirety).

Another exemplary lung system including the disclosed (alveolar) devices is illustrated in FIG. 12. In this FIG. 12, the top chamber includes branches or channels 152, 153 that comprise the top chamber. These branches communicate with the top surface of membrane sections 20, with the bottom surfaces of the membrane communicating with a liquid flow chamber with respective inlets and outlets (not shown but included in substrate block 180 that can be a bottom chamber structure as previously described.

In further embodiments, the devices disclosed herein (for example when integrated in a lung organ mimetic system) can be coupled to one or more additional organ mimetic systems, such as heart devices, liver devices, kidney devices, or the like.

Figure 14:
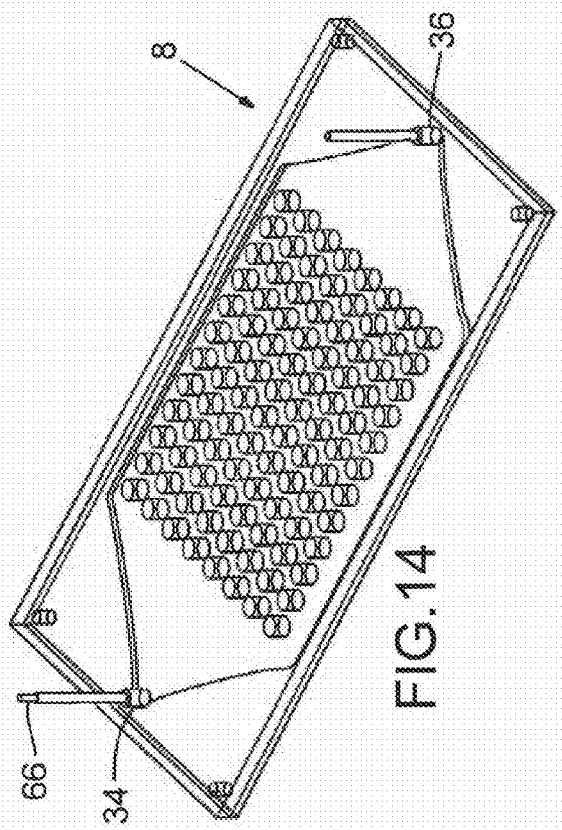
FIG. 14 is a perspective view of the assembled aspirator of FIG. 13.
Figure 15:
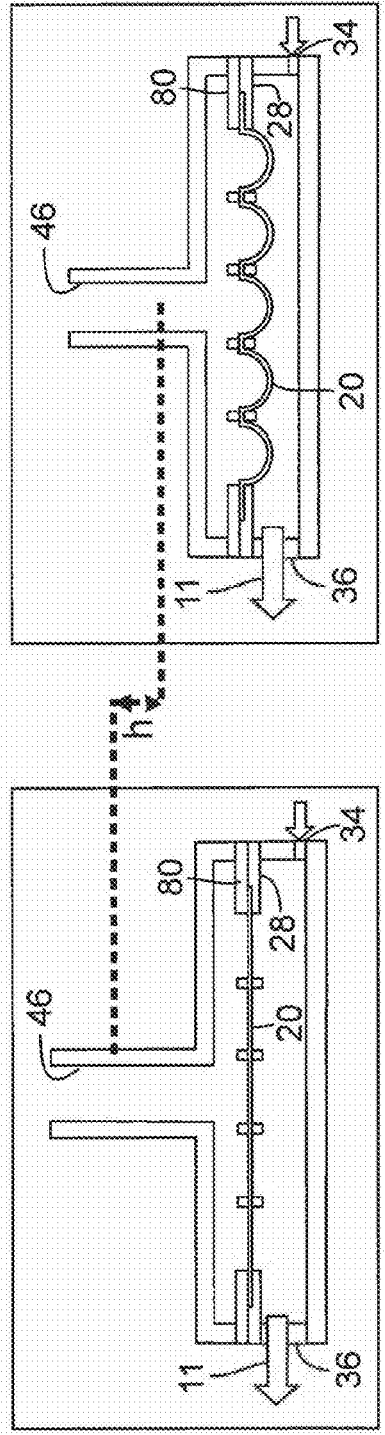
FIG. 15 is a schematic illustration showing use of an exemplary embodiment for measuring flow rate and/or viscosity of a fluid.

FIGS. 14 and 15 illustrate an aspirator with 96 wells or openings in substrates on either side of a membrane. The substrates can comprise plates. The substrates in the FIG. 14 embodiment in common with those in the FIG. 7 embodiment have been given the same numbers and will not be discussed further. In FIG. 14, the top chamber defining substrate 160 and top most substrate 170 have been omitted for clarity. In the embodiment of FIG. 14, the restriction 66 is located upstream of the inlet 34. In addition, the inlet 34 and the outlet 36 to and from the bottom chamber 14 extend downwardly through the substrates such that the port 46, inlet 34 and outlet 36 are all positioned for ready access at the same side of the aspirator. FIG. 15 illustrates the substrates of FIG. 14 in an exemplary assembled state.

III. Methods of Making the Devices

Disclosed herein are embodiments of methods for making the devices disclosed herein. In some examples, the methods include combining one or more components disclosed herein. In addition, methods of making the membranes utilized in the devices are disclosed.

In some embodiments, the disclosed devices are made using a plurality of substrates stacked on top of one another. At least one of the substrates is configured to accept a one or more inlets, outlets, or ports, for example for introducing or removing liquid and/or air or gas. For example, as illustrated in FIG. 7, a plurality of substrates, including top substrate (layer) 170, vacuum chamber substrate (layer) 160, top membrane frame (substrate) 150 with openings 82A-E, bottom membrane frame (substrate) 140 with openings 30A-30E, liquid chamber substrate (layer) 110, and bottom substrate (layer) 100. In some embodiments, membrane 20 is sandwiched between the two membrane frames or substrates 140, 150 and the membrane frames and membrane are incorporated into the device as a unit. The inlets, outlets, and ports of the substrates can be formed, for example, using a laser. In particular disclosed embodiments, one or more tube lines are attached, such as by using an adhesive, to the inlet and outlet of the liquid chamber layer. The tube lines can be attached at any point during making the device. The substrates are coupled together, for example using an adhesive or adhesive tape (single-sided and/or double-sided) and lamination or fasteners. In some examples, the device is assemble on an alignment stage, which includes one or more posts or pins that pass through the one or more alignment holes in each substrate to provide proper alignment of the components of each substrate or layer during assembly.

The substrates can be made of any suitable polymeric material capable, in the case of an exemplary lung device, of being fabricated to include the particular components of the bronchiolar device, such as channels, inlets, outlets, and chambers. In particular disclosed embodiments, the substrates include a polymer material, such as polydimethylsiloxane (PDMS), acrylic, polycarbonate, polyethylene terephthalate (PET), PET-G, Kapton, and/or polyether ether ketone (PEEK) materials. Each substrate can be made of the same or different material as each other substrate used in the device.

Additional methods of making the devices can be utilized, for example by separately fabricating top and bottom chambers and assembling them with a membrane between the chambers. The membrane can be fabricated as a separate layer and incorporated during device assembly or can be assembled as a unit with the top and bottom membrane frame substrates, for example to facilitate membrane handling (decreasing the risk of damage and facilitating additional manipulations, such as sterilization). In one embodiment, the membrane is placed on a first membrane frame including the desired number of openings. A second membrane frame, with the same number of openings is placed over the membrane with the openings in the first (bottom) membrane frame and the second (top) membrane frame being aligned. In some examples, the membrane is produced by spin coating; however, other techniques, such as spray coating, extrusion, or blown bubbles can also be utilized. In some examples, the membrane between the membrane frames includes a plurality of pores. In other examples, the membrane between the membrane frame is not initially porous and a plurality of pores are introduced in the membrane (for example, using a laser) prior to incorporating the membrane and membrane frames into the device.

One challenge of integrating membranes into microfluidic devices involves the difficulty of placing and fixing flexible membranes into planar systems. Although thin membranes can be fabricated in situ and assembled in a device, it is not trivial to integrate flexible membranes using common fabrication techniques available for microfluidics. Typically, membranes (such as PDMS membranes) are molded on a glass or silicon substrate. To remove a thin membrane from the substrate and incorporate it into a microfluidic device requires precise handling. The bonding between the substrate and the thin elastic membrane can be so strong that it makes the peeling step a challenge. Once the membrane is peeled off from the substrate, thin membranes (less than 50 µm) tend to crumple together and it is difficult to stretch the membranes back to their original state. These handling and fixation issues may decrease yield of usable membranes, cause instability, and eventually affect the function of the device in which it is incorporated. To address these challenges, in some examples, an exemplary method based on a combination of laser based micro-patterning and lamination techniques can be used to make the membranes and put them in a frame. This technique can allow peeling off the membrane from the substrate rapidly and easily using an adhesive layer or solvent (such as an alcohol), transporting the membrane with a membrane holder layer (e.g., a membrane frame) and the simpler and more effective integration of the membrane into the microfluidic device.

Thus, in some embodiments, a thin membrane (such as a polyurethane or PDMS membrane) is produced on a solid substrate using a spin coating technique. The membrane is peeled off the substrate, using water and/or alcohol (such as ethanol) to facilitate release of the membrane from the substrate and to reduce tearing. The membrane is placed on a second solid substrate and flattened and/or smoothed out. The membrane can then be transferred to a substrate that includes openings (such as a substrate 28, comprising one form of a substrate frame, with openings 30), for example, by placing the substrate or membrane frame on the membrane and lifting it from the solid substrate. If two membrane frames are used, a second membrane frame is aligned with the first membrane frame and placed over the membrane, sandwiching the membrane between the two frames. In examples where a porous membrane is desired, pores can be introduced in the membrane after transfer to the frame(s), for example using electromagnetic ablation, for example with a laser.

In some embodiments, a plurality of one or more types of cells is seeded on one or both sides of the membrane. In some examples, the cells are seeded on the membrane after assembly of the device (for example, by introducing cells into the device through one or more of the inlet or outlet of the bottom chamber and/or the port of the top chamber. In other examples, cells are seeded on one or both sides of the membrane prior to device assembly (for example, before or after the membrane is placed between the membrane frames).

IV. Methods of Using the Devices

The disclosed devices have numerous uses. In some embodiments, the devices are utilized as a model of lung alveolar function, or are integrated into a platform or system that mimics or models lung function. In other embodiments, the devices can be used in any application where formation of a vacuum is desired, for example with or without a port 46. Finally, the disclosed devices can be used in methods of determining flow rate and/or viscosity of a liquid and/or in tunable lens applications.

A. Alveolar or Lung Models

In some embodiments, the disclosed devices are used to independently model alveolar function and/or lung function (for example, as an alveolar component integrated into a lung model or platform). In some examples, the disclosed devices include a plurality of cells on one or both sides of the membrane, such as alveolar cells. The bottom chamber is filled with liquid (for example, substantially or completely filled with liquid). Liquid is flowed through the bottom chamber, creating a pressure drop due to the smaller size of the inlet than the outlet. This creates a vacuum in the top chamber causing air or gas intake into the top chamber through the port, and deformation of the membrane(s) into the liquid in the bottom chamber. When liquid flow in the bottom chamber is stopped the pressure equilibrates, causing the membranes to relax back to a resting position and air or gas to exit the top chamber through the port. The liquid flow can be pulsatile (repeated start and stop flow) to simulate breathing. Rather than totally stopping the liquid flow, the flow rate can be reduced to increase the pressure in the bottom chamber relative to the pressure in the bottom chamber that results from a higher flow rate. A first pump state can correspond to the higher flow rate and the second pump state can correspond to a flow rate lower than the higher flow rate. Alternatively, the flow rate can be reversed in the second pump state to more rapidly increase the pressure in the lower chamber. The rate of inhaling air into and exhaling air from the device can be varied by controlling the flow rates and flow direction.

In particular embodiments, a cell culture medium is utilized in the disclosed devices. The fluid includes components that support the viability and function of the plurality of cells one or both sides of the membrane in the device, including components such as inorganic salts and/or minerals, amino acids, energy-providing components, vitamins and/or cofactors, supplements, trace elements, organic acids, salts, and/or esters, antibiotics, and/or protein growth factors. In some examples, the cell culture medium includes those disclosed in International Pat. App. Publ. No. WO 2016/049367, which is incorporated herein by reference in its entirety.

In some embodiments, the disclosed devices are used to study drug (or drug candidate) efficacy and/or toxicity. Thus, in some examples, the devices (independently or integrated in a lung model) are used to study lung disorders, such as asthma, chronic obstructive pulmonary disease, cystic fibrosis, infectious diseases (such as influenza, pneumonia, or tuberculosis), lung cancer, and/or acute respiratory distress syndrome. In other examples, the disclosed devices are used to study the flow dynamics of particles in alveoli or lung. The disclosed devices can utilize the same pathway for air intake (inhalation) and outflow (exhalation), akin to a lung, and thus are more physiologically relevant than current organ-on-a-chip technologies, which utilize one-way airflow.

Particular method embodiments disclosed herein include introducing one or more compounds (such as a drug, toxin, stimulus, and/or infectious agent), into a device embodiment disclosed herein and analyzing a response generated after the compound has been introduced into the device. In some embodiments, the device is activated (for example, by cyclical creation and release of a vacuum) before, during, and/or after introducing the one or more compounds. The device may be used independently or integrated into a lung system or platform, as discussed above.

In some embodiments, analyzing a response includes detecting whether a compound causes a change in the way in which the device, or a component thereof, operates. In some embodiments, a control compound is introduced into the device to provide baseline results to be used as a comparison for other compounds of interest that are introduced into the device. Such control compounds may be any compound known to those of ordinary skill in the art to have a known or understood effect on lung activity (e.g., epinephrine, methoxamine, or the like) or may be an inert compound or composition (e.g., buffer or carrier). For example, in some embodiments, the compound can adversely influence or modify one or more of the cell populations associated with various components of the device (e.g., a membrane material) so that the cell population produces responses (e.g., immune responses, physical leakage of fluids between a membrane layer, changes in gene expression, secretion of molecules, cell death or apoptosis, cellular edema, inhibition of gas exchange, or a combination thereof) that can be detected using a suitable detection technique, such as immunohistochemical staining, trans-epithelial electric resistance (TEER) measurements, visual detection, mass spectrometric detection, chromatographic detection or the like.

In some embodiments, a first compound that has any of the above-mentioned adverse effects on one or more components of the device is introduced and then a second compound, such as a therapeutic compound (or potentially therapeutic compound) capable of ameliorating, inhibiting, or stopping the adverse effects, is introduced. The ability of the second compound to ameliorate or stop the adverse effects is them determined by analyzing a sample extracted from the device and determining whether, for example, leakage has been stopped or reduced or if immune responses from the cell populations have stopped or diminished.

The disclosed devices or lung organ devices including the disclosed devices can be further combined with one or more analytical devices capable of analyzing samples obtained from the device. Such devices can be used to analyze a response generated by the lung organ device. For example, devices like chromatographs (gas or liquid), mass spectrometers, or a combination thereof can be used to analyze fluids that are extracted from the lung organ device to detect or determine the presence of drugs, toxins, or other chemical components present in the fluids. In some embodiments, fluids may be extracted from the device using an automated system. The analytical devices can be integrated with or separate from the device, or a component thereof.

B. Vacuum on a Chip

As discussed above, the disclosed devices utilize a pressure drop produced by flow restriction upstream of a bottom chamber, such as at an inlet to the bottom chamber, to mimic lung function by creating a vacuum in the top chamber ("inhaling") and releasing the vacuum to equilibrate pressure ("exhaling").

Figure 18:
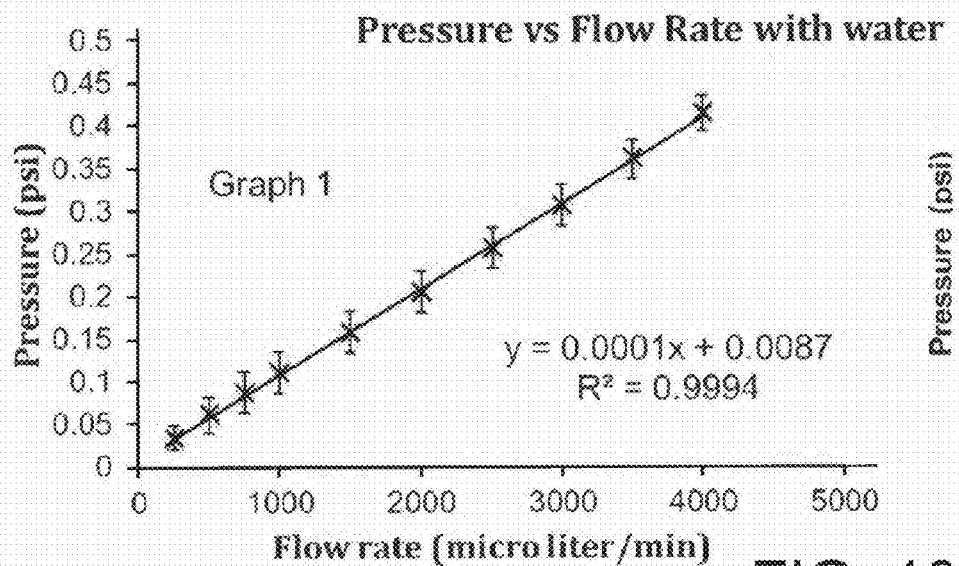
FIG. 18 is a graph showing pressure versus flow rate for water.

However, the disclosed devices can be utilized in any situation where it is desirable to apply a vacuum, essentially acting as a milli- or micro-scale vacuum pump. As illustrated in FIG. 18, in one non-limiting example, the vacuum achieved is proportional to the flow rate in the bottom chamber. A vacuum of up to −68 kPa has been produced in a 27 µl device with N=5 (for example, as illustrated in FIG. 8C at the highest performance. In a vacuum pump application the membrane is typically not provided with pores.

In some embodiments, one end of a connector (such as tubing) is attached to a port 46 communicating with the top chamber and the other end of the connector is attached to a device in which it is desired to create a vacuum. Vacuum is created by flowing liquid through the bottom chamber of the device, creating a pressure drop in the bottom chamber and a vacuum in the upper chamber. The strength of the vacuum can be adjusted, for example by increasing or decreasing the fluid flow rate. The vacuum is released by stopping fluid flow in the lower chamber.

In some examples, the disclosed devices can be used to create suction, decrease pressure in a chamber (such as a chamber in a microfluidic device or system), or other applications. In one example, the disclosed devices can be used to provide vacuum in a miniaturized (for example, portable) mass spectrometer.

C. Flow and Viscosity Measurement

In some embodiments, the disclosed devices are used in methods of measuring flow (such as flow rate) and/or viscosity of a liquid. The microfluidic aspiration and membrane deformation in the device is a function of the liquid flow rate in the bottom chamber of the device, as well as the viscosity of the fluid in the bottom chamber of the device.

In one example, for a rectangular channel (such as that shown in FIG. 15), pressure drop inside the channel can be described as:

$$\Delta P = \frac{12\mu LQ}{h^3 w}$$

where ΔP is pressure drop in the device caused by flow restriction; μ is the viscosity of the liquid; Q is the flow rate; L is the chamber length; h is the chamber height; and w is the chamber width. Thus, viscosity of liquid in the bottom chamber can be calculated if pressure drop, flow rate, and chamber length, height, and width are known. Likewise, the flow rate of the liquid can be calculated if pressure drop, liquid viscosity, and chamber length, height, and width are known.

Figure 16:
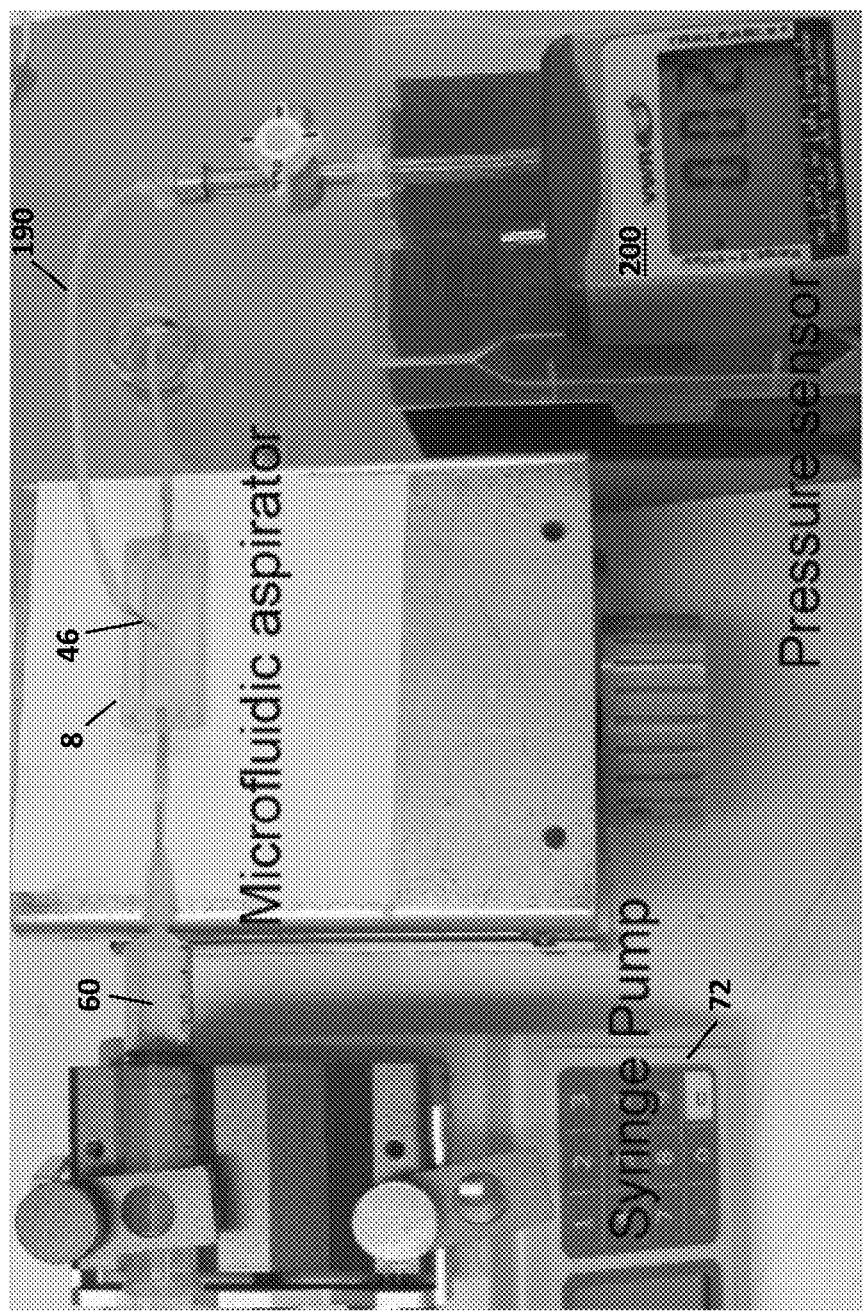
FIG. 16 is a perspective view of an aspirator in accordance with this disclosure having a top chamber port coupled to a pressure sensor for use in, for example, viscosity measurements or flow rate determinations.
Figure 17:
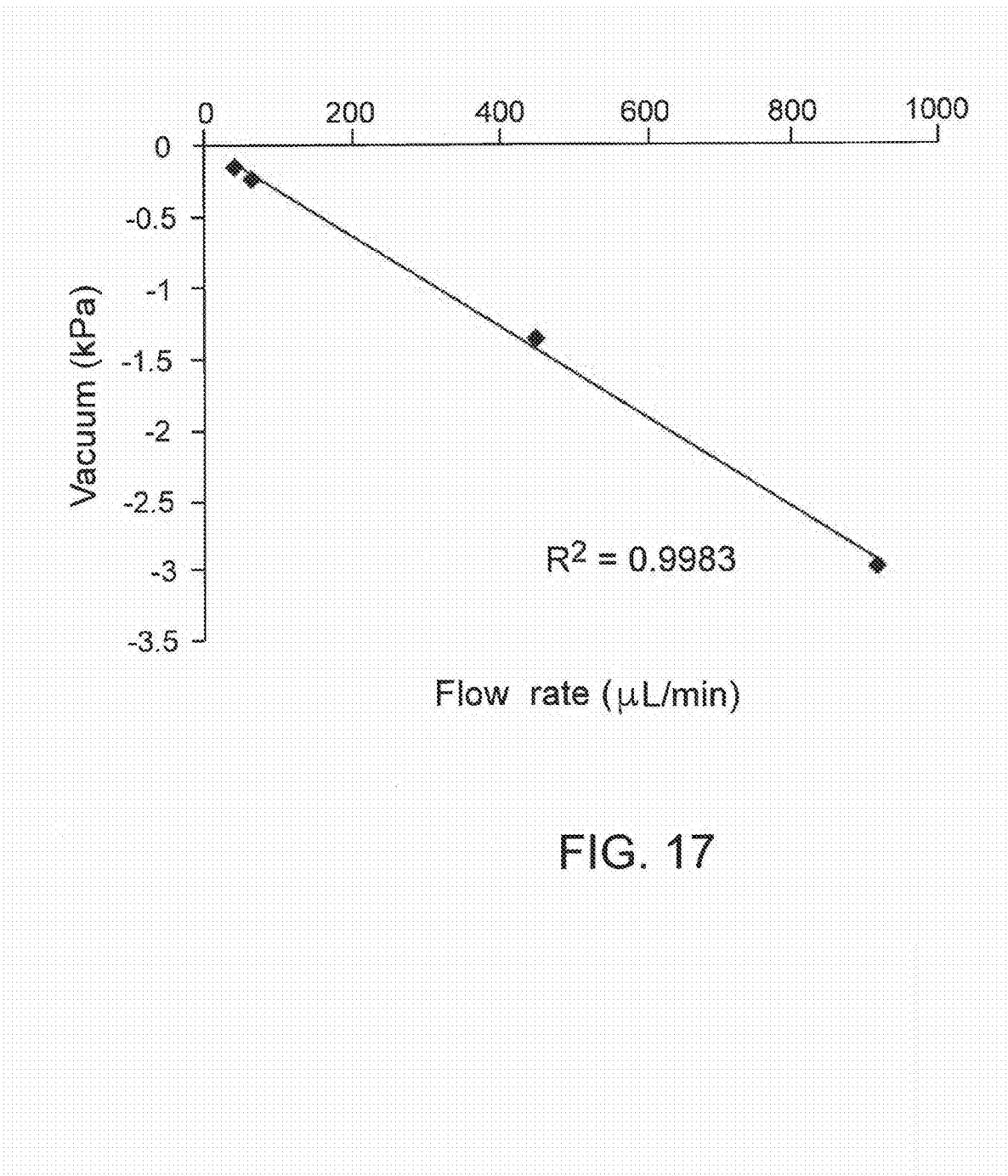
FIG. 17 is a graph showing the effect of flow rate on vacuum in an exemplary embodiment.
Figure 19:
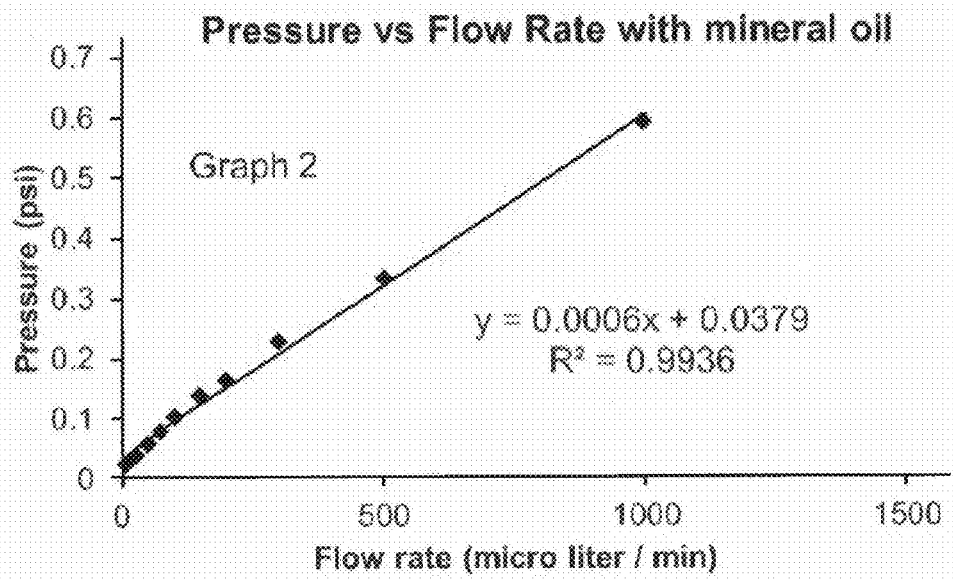
FIG. 19 is a graph showing pressure versus flow rate for mineral oil.

As shown in FIG. 16, a pressure sensor can be connected to the port 46 communicating with the top chamber to measure the pressure drop caused by changes in the liquid flow rate through the lower chamber. Since the chamber dimensions are known, by measuring the pressure drop during liquid flow, the flow rate for a given viscosity liquid can be determined. Alternatively, the viscosity of a liquid for a given flow rate can be determined. FIG. 18 is a graph of pressure versus liquid flow rate for water. FIG. 19 is a graph of pressure versus liquid flow rate for mineral oil. This data is from the operation of a five well version (the aspirator of FIG. 8C) with a 35 μm PDMS pore free membrane and openings 30 A-E and 82 A-E that were 4 mm. The data shown in FIG. 17 was also obtained from operation of this device.

In other examples, the top chamber 12 of the aspirator device is filled with a liquid (for example, a liquid containing a dye), such that the liquid at least partly extends into the port 46. In some examples, the port may be longer and/or wider than in devices utilized in other uses herein, for example, to better visualize the meniscus formed by the liquid in the top chamber. Displacement of the meniscus of the liquid in the top chamber can be observed during flow of liquid through the bottom chamber. The displacement of the meniscus is proportional to the flow rate of the liquid in the bottom chamber for a given viscosity and is proportional to viscosity of the liquid in the bottom chamber for a given flow rate.

The disclosed devices can be utilized as a flow or viscosity sensor for any fluidic or microfluidic applications. In some examples, the disclosed devices can be included in a microfluidic chip or system (such as those described in International Pat. App. Publ. Nos. WO 2016/049363 and WO 2016/049365) to provide an integrated flow and/or viscosity sensor. In some examples, the flow and/or viscosity sensor element (such as the disclosed device) includes one or more sensors (such as a pressure sensor or optical sensor) that receives input from the device. The device and/or the sensors can be connected to an electronic module (such as a computer) that receives information and provides an output, such as a flow or viscosity reading. In some examples, the electronic module may also be utilized to set operating conditions, such as flow rate or to stop and start flow. These parameters can be manually, semi-automatically, or automatically controlled.

D. Tunable Lens

With reference to FIG. 20 and FIGS. 21-23, an application of the technology disclosed herein to tuning or adjusting the focal point of a lens is described.

Figure 20:
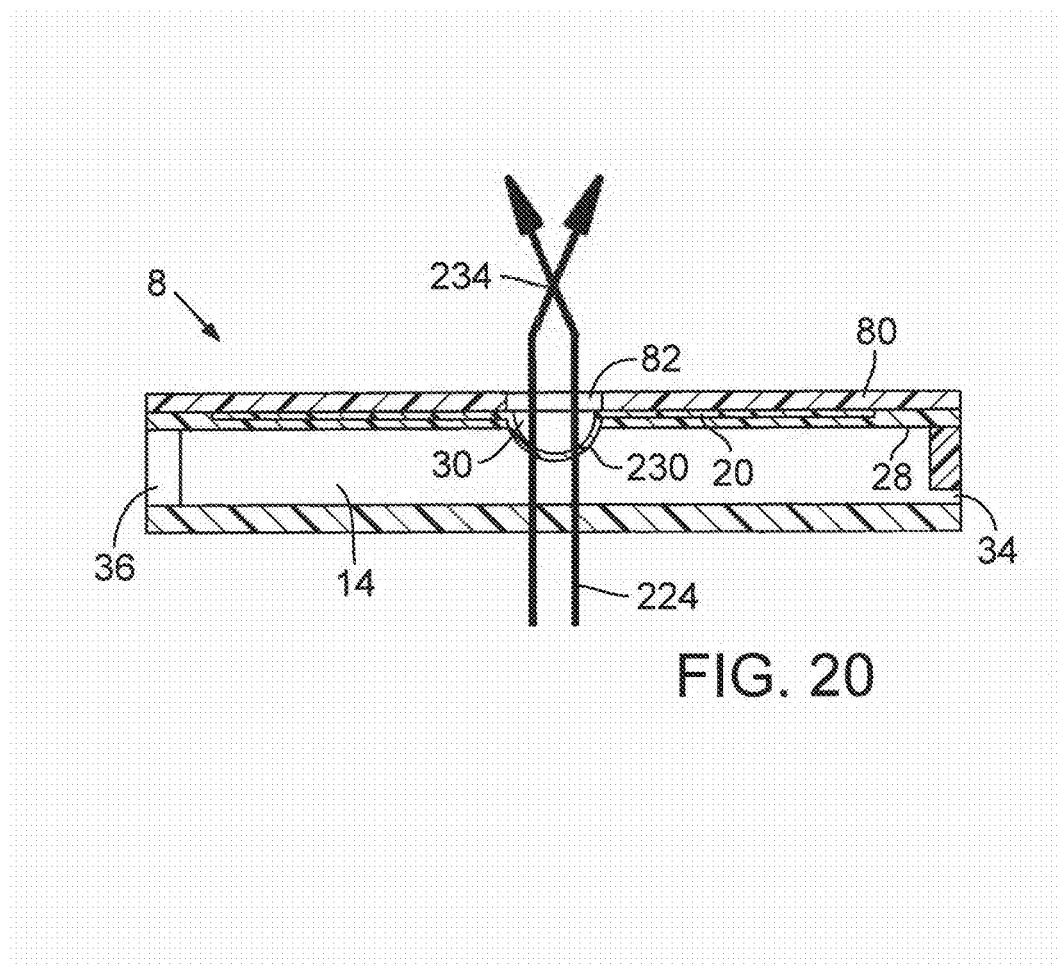
FIG. 20 shows an aspirator in accordance with this disclosure modified for use as a tunable lens.

In FIG. 20, the top chamber 12 is eliminated and a bottom liquid flow chamber 14 with at least one inlet 34 and at least one outlet 36 is disclosed. A flow restriction as previously described is placed at or upstream of the inlet 34 to chamber 14. The bottom wall of the bottom chamber is light trans-missive and/or includes a light trans-missive section, such as of glass or polymer material. Light 224 is shown passing upwardly through the bottom wall of the bottom chamber. The membrane 20 comprises a lens, and is positioned as previously described between, in this example, substrates 28 and 80. The light 224 is shown passing upwardly through openings 30 and 82 and through a lens 230 (a portion of membrane 20) between substrates 28, 80 in FIG. 20. With liquid flow stopped, the lens 230 is relaxed to a planar state and is positioned perpendicular to the path of light 224 through the lens 230. In response to liquid flow through the chamber 14 from the inlet 34 to the outlet 36, pressure drops in the chamber 14. As a result, the membrane 20 bulges toward chamber 14 as shown in FIG. 20. The extent of the bulging corresponds to the pressure drop in chamber 14 and to the flow rate of liquid. The lens is shown to have a hypothetical focal point at 234. Desirably the openings 30, 82 are circular so that the lens becomes a convex spherical lens as it bulges inwardly in this example. By changing the extent of bulging, the focal length can be changed.

Figure 21:
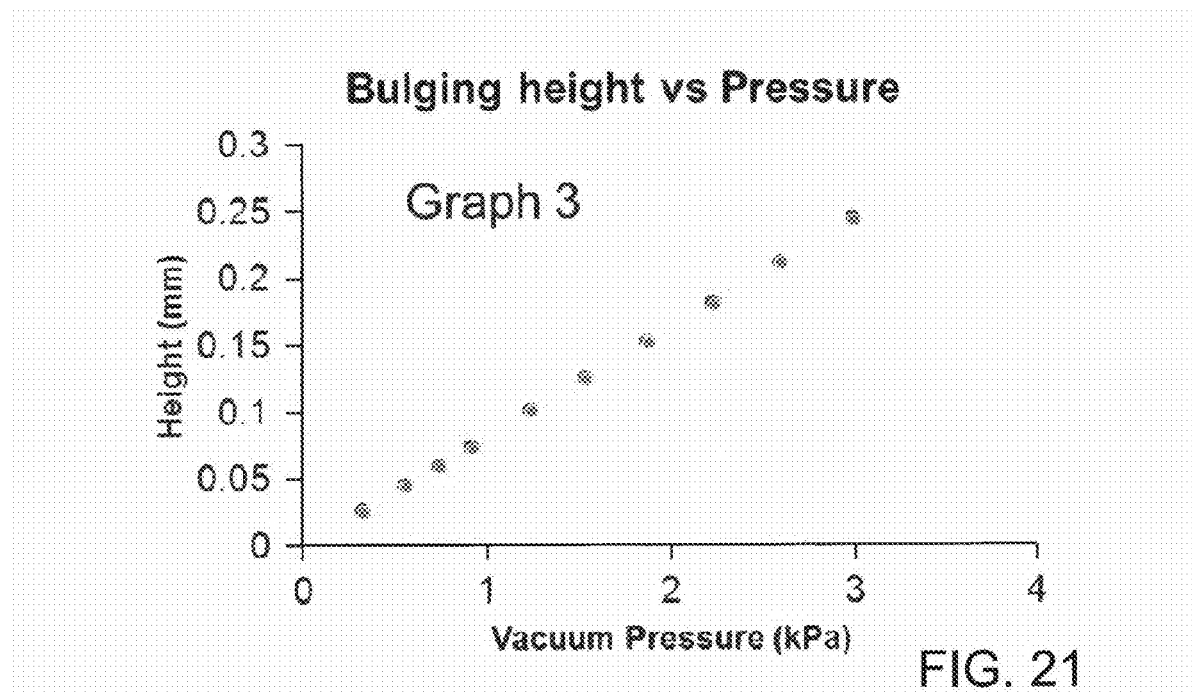
FIG. 21 is a graph showing lens bulging height versus pressure.
Figure 22:
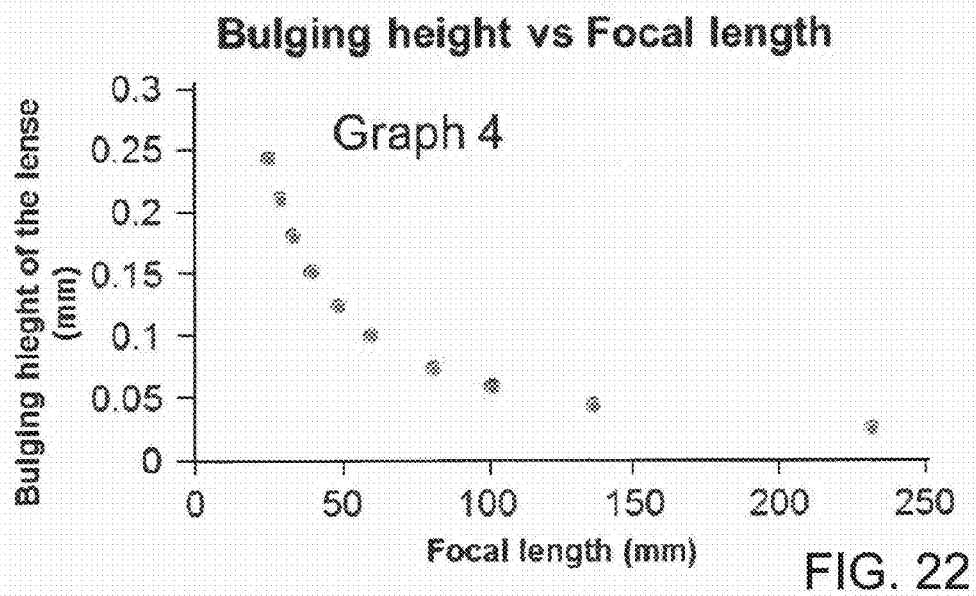
FIG. 22 is a graph showing bulging height versus focal length.
Figure 23:
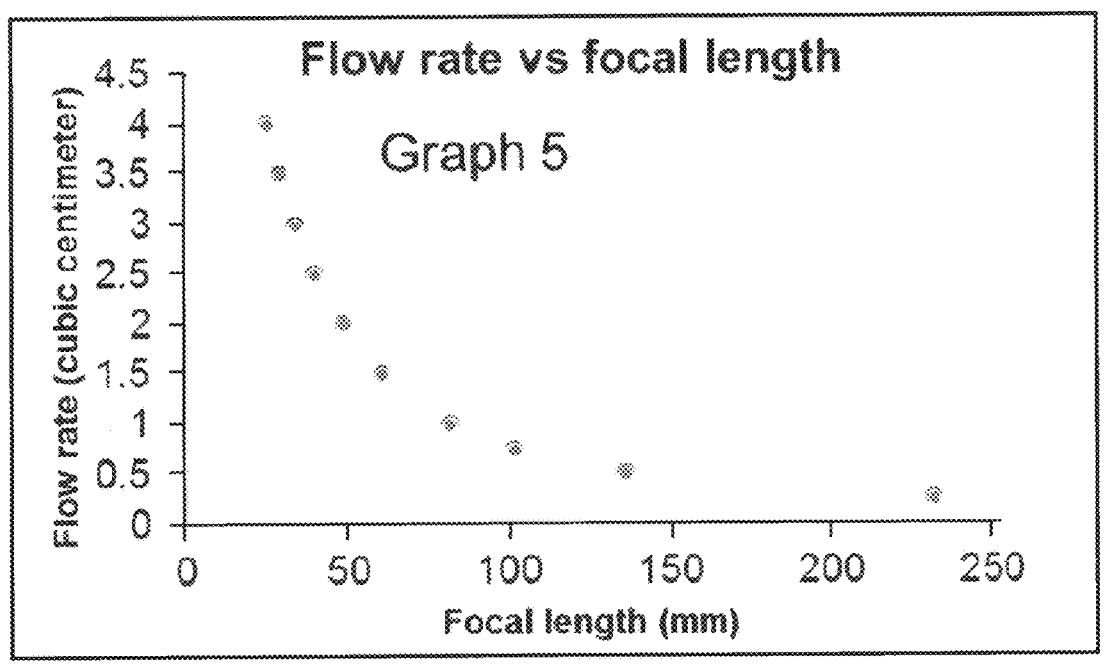
FIG. 23 is a graph showing flow rate versus focal length.

The term bulging height refers to the distance the most distal portion (typically the center of the lens) of the lens has moved from its relaxed position. FIG. 21 illustrates an example of a graph of bulging height versus pressure in chamber 14. By changing the pressure drop (vacuum) in chamber 14, one can vary the bulging height and change the focal length and tune the lens to the desired focal length. FIG. 22 illustrates an example of a graph of focal length versus bulging height for the apparatus of FIG. 20. Finally, FIG. 23 is a graph of flow rate versus focal length for the apparatus of FIG. 20. As one can see, controlling the flow rate, by for example controlling the rate of pumping liquid by a pump coupled to the outlet 36, one can control the focal length and tune the lens 230. The data in FIGS. 21-23 is based on calculations from pressure versus flow rate and experimental data.

In view of the many possible embodiments to which the principles of the disclosure may be applied, it should be recognized that the illustrated embodiments are only examples and should not be taken as limiting the scope of the invention. Rather, the scope of the invention includes all novel and non-obvious combinations and sub-combinations of elements set forth herein. We therefore claim as our invention all that comes within the scope and spirit of the following claims.

We claim:

1. An apparatus comprising:
 a housing comprising a top chamber comprising at least one port and a bottom chamber comprising at least one inlet and at least one outlet; and
 a membrane comprising a boundary edge and first and second side surfaces, at least a portion of the first side surface of the membrane being fluidly coupled to the bottom chamber and at least portions of the second side surface of the membrane being fluidly coupled to the top chamber;

wherein the bottom chamber further comprises:
(i) a first section connected to the inlet, a second section connected to the outlet, and at least one intermediate section between the inlet and the outlet, wherein:
the cross sectional area of the first section is smaller at a first location than at a second location spaced further from the at least one inlet than the first location,
the cross sectional area of the second section is smaller at a third location than at a fourth location positioned further from the at least one outlet than the third location, and
the total cross sectional diameter of the at least one inlet is smaller than the total cross sectional diameter of the at least one outlet; and
(ii) first and second bottom chamber side walls, a bottom chamber bottom wall and a bottom chamber top wall, wherein the bottom chamber top wall comprises:
a first membrane-supporting first substrate positioned to support the first side surface of the membrane, wherein the first membrane-supporting first substrate comprises at least one first substrate opening into which the membrane expands in response to a pressure drop in the bottom chamber relative to the pressure in the top chamber, and
a second substrate that overlays the first substrate, wherein the second substrate comprises at least one second substrate opening aligned with the at least one first substrate opening, wherein in response to the elimination of the pressure drop in the bottom chamber relative to the pressure in the top chamber, the membrane moves toward the at least one second substrate opening.

2. An apparatus according to claim 1 wherein the cross sectional area of the inlet, and all of the inlets if there is more than one inlet is less than the cross sectional area of the at least one intermediate section.

3. An apparatus according to claim 1 wherein the cross sectional area of the first section progressively increases moving away from the at least one inlet, and wherein the cross sectional area of the second section progressively decreases moving toward the at least one outlet.

4. An apparatus according to claim 1 the first and second sections of the bottom chamber being bounded by respective portions of the first and second bottom chamber side walls, a respective portion of the bottom chamber bottom wall and a respective portion of the bottom chamber top wall, at least portions of the first and second side walls bounding the first section diverging from one another moving away from the at least one inlet, and at least portions of the first and second side walls bounding the second section converging toward one another moving toward the at least one outlet.

5. An apparatus according to claim 1 wherein the at least one port is open to the atmosphere such that expansion of the membrane into the first substrate opening inhales air into the top chamber from the atmosphere and movement of the membrane toward the at least one second substrate opening exhales air outwardly from the top chamber through the port.

6. An apparatus according to claim 5 comprising a population of cells on at least a portion of at least one of the first and second side surfaces and wherein the bottom chamber contains a liquid cell culture medium.

7. An apparatus according to claim 6 comprising a source of liquid cell culture medium coupled to the at least one inlet, a pump coupled to the at least one outlet;

the apparatus comprising an upstream to downstream liquid flow path from the source of liquid cell culture medium downstream to the at least one inlet, through the bottom chamber to the at least one outlet and from the at least one outlet to the pump;
wherein in a first pump state, the pump operates to pump the liquid cell culture medium from the at least one outlet of the bottom chamber and reduces the pressure in the bottom chamber relative to the pressure in top chamber so that the membrane moves into the first substrate opening and inhales air from the at least one port into the upper chamber;
and wherein in a second pump state the pump stops pumping the liquid cell culture medium from the at least one outlet of the bottom chamber and increases the pressure in the bottom chamber relative to the pressure in the bottom chamber when the pump is in the first pump state so that the membrane moves toward the at least one second substrate opening and exhales air outwardly from the upper chamber through the at least one port.

8. An apparatus according to claim 7 wherein the pump is cycled between the first and second pump states a plurality of times to cause the repeated inhaling of air through the at least one port into the top chamber and the exhaling of air from the top chamber through the at least one port.

9. An apparatus according to claim 8 wherein the cells are alveolar cells.

10. An apparatus according to claim 1 wherein the membrane comprises a polymer with a plurality of pores from the first side surface to the second side surface of the membrane.

11. An apparatus according to claim 1 comprising:
a bottom chamber bottom wall substrate;
a bottom chamber intermediate substrate overlaying the bottom chamber bottom wall substrate and having bottom chamber side walls that surround the bottom chamber;
a bottom chamber top wall substrate overlaying the bottom chamber intermediate substrate, the bottom chamber top wall substrate comprising a plurality of spaced apart openings, the bottom chamber top wall substrate having an upper surface positioned to engage the first side surface of the membrane with the membrane overlaying the plurality of spaced apart openings;
a top chamber bottom wall substrate overlaying the second side surface of the membrane and comprising a plurality of spaced apart openings overlaying the spaced apart openings of the bottom chamber top wall substrate;
a top chamber intermediate substrate overlaying the top chamber bottom wall substrate and having top chamber side walls that surround the top chamber;
and a top chamber top substrate overlaying the top chamber intermediate substrate.

12. An apparatus comprising:
a housing comprising a top chamber comprising at least one port and a bottom chamber comprising at least one inlet and at least one outlet;
a membrane comprising a boundary edge and first and second side surfaces, at least a portion of the first side surface of the membrane being fluidly coupled to the bottom chamber and at least portions of the second side surface of the membrane being fluidly coupled to the top chamber;
a pump coupled to the at least one outlet;
the apparatus comprising an upstream to downstream liquid flow path adapted for coupling to a source of liquid that is upstream from the at least one inlet, the liquid flow path passing from the at least one inlet, through the bottom chamber to the at least one outlet and from the at least one outlet to the pump;

the liquid flow path having a section of reduced cross sectional area upstream of the at least one inlet to the bottom chamber;

wherein in a first pump state, the pump operates to pump the liquid from the at least one outlet of the bottom chamber at a first flow rate and reduces the pressure in the bottom chamber relative to the pressure in top chamber and moves the membrane toward the bottom chamber;

and wherein in a second pump state the pump stops pumping the liquid from the at least one outlet of the bottom chamber or pumps liquid from the outlet at a second flow rate less than the first flow rate and increases the pressure in the bottom chamber relative to the pressure in the top chamber when the pump is in the first pump state and moves the membrane away from the bottom chamber.

13. An apparatus according to claim 12 comprising a first membrane supporting first substrate positioned to support the first side surface of the membrane, the first membrane supporting first substrate comprising at least one first substrate opening into which the membrane moves in response to the reduction in the pressure in the bottom chamber relative to the pressure in the top chamber when the pump is in the first pump state, and wherein a second substrate overlays the first substrate, the second substrate comprising at least one second substrate opening aligned with the at least one first substrate opening, wherein in response to the increase in pressure in the bottom chamber relative to the pressure in the top chamber when the pump is in the second pump state, the membrane moves toward the at least one second substrate opening.

14. An apparatus according to claim 12 further comprising a source of liquid cell culture medium coupled to the at least one inlet as the source of liquid.

15. An apparatus according to claim 14 comprising a population of cells on at least a portion of at least one of the first and second side surfaces of the membrane.

16. An apparatus according to claim 12 wherein in the second pump state, the pump stops pumping the liquid from the at least one outlet.

17. An apparatus according to claim 15 wherein the port is open to the atmosphere and wherein the pump cycles between the first and second pump states a plurality of times to respectively inhale air into the top chamber through the port and exhale air from the top chamber through the port.

18. An apparatus according to claim 12 further comprising a pressure sensor coupled to the port to sense the pressure in the top chamber.

19. A method of maintaining a population of cells along at least one surface of a membrane, the method comprising:

pumping liquid cell culture medium through the bottom chamber of the apparatus of claim 1 to reduce the pressure in the bottom chamber and expand the membrane into the bottom chamber;

stopping the pumping of liquid cell culture medium through the bottom chamber to thereby relax the membrane and move the membrane toward the top chamber; and inhaling air into the top chamber in response to the expansion of the membrane into the bottom chamber and exhaling air from the top chamber in response to the relaxation of the membrane, wherein at least one of the side surfaces of the membrane supports the population of cells.

20. A method of maintaining a population of cells, the method comprising:

pumping liquid cell culture medium through the bottom chamber of the apparatus of claim 12 to reduce the pressure in the bottom chamber and expand the membrane into the bottom chamber;

stopping the pumping of liquid cell culture medium through the bottom chamber to thereby relax the membrane and move the membrane toward the top chamber; and inhaling air into the top chamber in response to the expansion of the membrane into the bottom chamber and exhaling air from the top chamber in response to the relaxation of the membrane, wherein at least one of the side surfaces of the membrane supports the population of cells.

* * * * *